(12) United States Patent
Khopade et al.

(10) Patent No.: US 10,172,852 B2
(45) Date of Patent: Jan. 8, 2019

(54) METHOD OF INCREASING BIOAVAILABILITY AND/OR PROLONGING OPHTHALMIC ACTION OF A DRUG

(71) Applicant: Sun Pharma Advanced Research Company Limited, Mumbai (IN)

(72) Inventors: Ajay Jaysingh Khopade, Baroda (IN); Arindam Halder, Baroda (IN)

(73) Assignee: SUN PHARMA ADVANCED RESEARCH COMPANY LTD., Maharashtra (IN)

( * ) Notice: Subject to any disclaimer, the term of this patent is extended or adjusted under 35 U.S.C. 154(b) by 0 days.

(21) Appl. No.: 15/329,824

(22) PCT Filed: Jul. 24, 2015

(86) PCT No.: PCT/IN2015/050076
§ 371 (c)(1),
(2) Date: Jan. 27, 2017

(87) PCT Pub. No.: WO2016/016908
PCT Pub. Date: Feb. 4, 2016

(65) Prior Publication Data
US 2017/0239243 A1    Aug. 24, 2017

(30) Foreign Application Priority Data

Jul. 28, 2014 (IN) .......................... 2437/MUM/2014
Jun. 9, 2015 (IN) .......................... 2206/MUM/2015

(51) Int. Cl.
*A61K 31/498* (2006.01)
*A61K 9/16* (2006.01)
*A61K 9/00* (2006.01)
*A61K 9/08* (2006.01)
*A61K 9/51* (2006.01)
(Continued)

(52) U.S. Cl.
CPC .......... *A61K 31/498* (2013.01); *A61K 9/0048* (2013.01); *A61K 9/0051* (2013.01); *A61K 9/08* (2013.01); *A61K 9/1635* (2013.01); *A61K 9/5176* (2013.01); *A61K 45/06* (2013.01); *B01J 39/20* (2013.01)

(58) Field of Classification Search
None
See application file for complete search history.

(56) References Cited

U.S. PATENT DOCUMENTS 7,001,615 B1 * 2/2006 Singh ................... A61K 9/0043
424/486
2005/0181017 A1 * 8/2005 Hughes ................ A61K 9/0048
424/427

* cited by examiner

*Primary Examiner* — Aradhana Sasan
(74) *Attorney, Agent, or Firm* — Davidson, Davidson & Kappel, LLC

(57) ABSTRACT

The present invention relates to a method of increasing the bioavailability and/or prolonging ophthalmic action of a drug, the method comprising instilling into the eye an aqueous suspension comprising reversible clusters of drug loaded nano-resin particles, said clusters having a D50 value of at least 2 micrometer and said drug loaded nano-resin particles have a particle size distribution characterized in that the D90 value is 70 nanometer to 900 nanometer. The present invention further relates to an aqueous suspension comprising reversible clusters of drug loaded nano-resin particles, said clusters have a D50 value of at least 2 micrometers and said drug loaded nano-resin particles have a particle size distribution characterized in that the D90 value is 70 nanometers to 900 nanometers.

19 Claims, 10 Drawing Sheets

(51) Int. Cl.
*A61K 45/06* (2006.01)
*B01J 39/20* (2006.01)

METHOD OF INCREASING BIOAVAILABILITY AND/OR PROLONGING OPHTHALMIC ACTION OF A DRUG

FIELD OF INVENTION

The present invention relates to a method of increasing the bioavailability and/or prolonging ophthalmic action of a drug, the method comprising instilling into the eye an aqueous suspension comprising (a) reversible clusters of drug loaded nano-resin particles, said clusters having a $D_{50}$ value of at least 2 micrometer and said drug loaded nano-resin particles have a particle size distribution characterized in that the $D_{90}$ value is 70 nanometer to 900 nanometer, and (b) a suspending agent.

The present invention also relates to an aqueous suspension comprising (a) reversible clusters of drug loaded nano-resin particles, said clusters have a $D_{50}$ value of at least 2 micrometers and said drug loaded nano-resin particles have a particle size distribution characterized in that the $D_{90}$ value is 70 nanometers to 900 nanometers, and (b) a suspending agent.

BACKGROUND OF THE INVENTION

Ophthalmic drug delivery is one of the most challenging endeavors facing the pharmaceutical scientist. The eye is a unique organ, both anatomically and physiologically, containing several widely varied structures with independent physiological functions. The complexity of the eye provides unique challenges to drug delivery strategies. Typically, the ocular bioavailability of drugs applied topically as eye-drops is very poor. The absorption of drugs in the eye is severely limited by some protective mechanisms that ensure the proper functioning of the eye, and by other concomitant factors, for example: nasolacrimal drainage of the instilled solutions; lacrimation and tear turnover; low corneal contact time; metabolism; tear evaporation; non-productive absorption/adsorption; limited corneal area and poor corneal permeability; and binding by the lacrimal proteins. These factors have a huge effect on ocular drug absorption and disposition and lead to low ocular drug bioavailability. Thus, developing an ocular drug delivery system that provides optimum drug bioavailability is a challenge. It is important to consider a number of factors, including effective corneal application to promote good corneal penetration, prolonged contact time with the corneal epithelium and the use of a formulation with appropriate rheological properties that is non-irritable to the eye. This challenge becomes all the more difficult in case of diseases that are associated with tissues at posterior segment of the eye such as diabetic retinopathy, glaucomatous optic neuropathy, age-related macular degeneration etc., which are very difficult to treat. Methods used for ocular drug delivery for the front of the eye or anterior segment differ significantly and pose considerably less risk than subcutaneous or posterior segment eye therapy. Methods available for posterior segment drug delivery are complex, for instance injections in the desired posterior tissue, sustained-release implants, iontophoretic drug delivery etc. and these can be associated with greater risk of infection, internal ocular bleeding and retinal damage. The conventional ophthalmic solutions, suspensions and ointment dosage forms are no longer sufficient for combating some present virulent diseases of the anterior segment as well as diseases affecting the posterior segment of the eye. Moreover, the conventional formulations have another disadvantage that they necessitate frequent administrations, sometimes four to five times a day in order to provide desired therapeutic effect, which leads to patient non-compliance.

Few advance ocular delivery systems have been commercialized recently or are under development, with an aim at enhancing the drug bioavailability either by providing sustained delivery to the eye or by facilitating transcorneal penetration. Advances in recent years in topical ocular drug delivery have ranged from iontophoretic drug delivery, in situ gelling systems, dendrimers, penetration enhancers, lipid emulsions, ocular inserts, and site-specific drug delivery systems. Nonetheless, very few drug delivery systems have successfully appeared on the market: currently, about 95% of the products are delivered via the traditional eye-drop bottle. There is a continuing need for developing efficient ophthalmic drug delivery systems/formulations which overcomes the aforesaid problems. There is a need for efficient ophthalmic drug delivery systems which upon ocular administration, leads to increase in ocular bioavailability of the drug both in the anterior as well as posterior segment of the eye, prolonging the ophthalmic action of the drug, and minimizing the irritation or other discomfort associated with ocular application.

The present invention fulfills this need and provides a novel ophthalmic drug delivery system in the form a novel aqueous suspension comprising nano-resin particles. The present invention provides a method of increasing the bioavailability and/or prolonging the ophthalmic action of a drug, by instilling the novel aqueous suspension of the present invention into the eyes. The ability of the present invention to deliver the drug in the posterior segment of the eye make it suitable for treating diseases of the posterior segment, which are difficult to treat.

SUMMARY OF THE INVENTION

The present invention provides a method of increasing the bioavailability and/or prolonging ophthalmic action of a drug, the method comprising instilling into the eye an aqueous suspension comprising (a) reversible clusters of drug loaded nano-resin particles, said clusters having a $D_{50}$ value of at least 2 micrometer and said drug loaded nano-resin particles have a particle size distribution characterized in that the $D_{90}$ value is 70 nanometer to 900 nanometer, and (b) a suspending agent.

The present invention further provides an aqueous suspension comprising (a) reversible clusters of drug loaded nano-resin particles, said clusters have a $D_{50}$ value of at least 2 micrometers and said drug loaded nano-resin particles have a particle size distribution characterized in that the $D_{90}$ value is 70 nanometers to 900 nanometers, and (b) a suspending agent.

The present invention also provides a method of increasing the bioavailability and/or prolonging ophthalmic action of a drug, the method comprising providing an aqueous suspension comprising (a) reversible clusters of drug loaded nano-resin particles, said clusters having a $D_{50}$ value of at least 2 micrometers and said drug loaded nano-resin particles having a particle size distribution characterized in that the $D_{90}$ value is 70 nanometers to 900 nanometers, and (b) a suspending agent

DETAILED DESCRIPTION OF THE INVENTION

Figure 1:
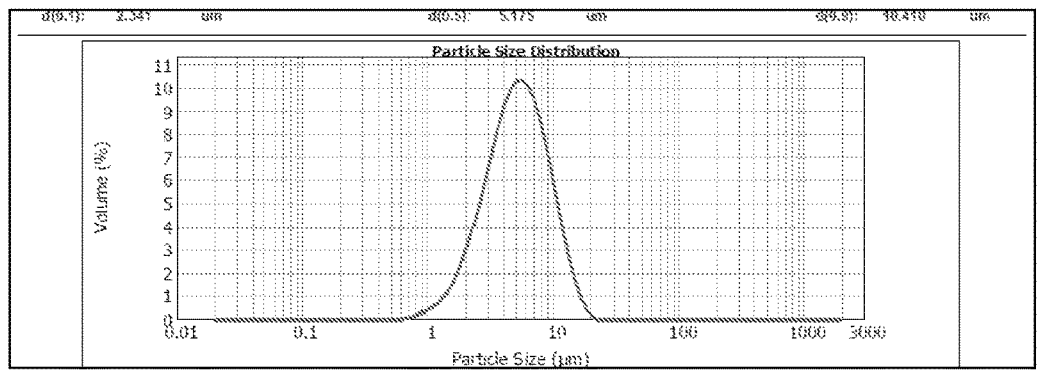
FIG. 1 is an illustrative histogram for the resin particles having mean particle size of 5 microns used in the preparation of suspension of comparative example 1.

'Reversible Clusters' of drug loaded nano-resin particles, according to the present invention means that the individual drug loaded nanoresin particles form aggregates or agglomerates having mean size of about 2 micrometers or greater which upon application of shear deagglomerate or decluster into individual drug loaded nano-resin particles.

Inventors have found that such reversible clusters decluster upon application of shear such as that resulting from the blinking of the eye.

Qualitatively, the declustering can be observed by microscopy (Morphology G3S-ID Instrument, Make: Malvern) by observing sheared (by smearing) and unsheared samples onto the glass slide.

As referred to further herein, the $D_{50}$ of the clusters is obtained from the particle size distribution obtained before the application of shear. The particle size distribution may be determined in a suitable particle size analyser such as the Malvern Mastersizer. The particle size analyser's sonication means are not used but the sample is only subjected to stiffing by a mechanical stirrer.

The suspension of clusters is placed in a sonication bath and is subjected to shear using sonication frequency of about 33±3 kHz for 5 seconds, and a sample withdrawn to measure the particle size distribution. Following intervals of 1 minute each the process is repeated 5 times. (See Example 7, FIGS. 9-14)

Nanoresin particles or drug-loaded nanoresin particles according to the present invention means individual ion exchange resin particles and not clusters or agglomerates of the individual particles which individual particles have a particle size distribution characterized in that the $D_{90}$ value is in the range of about 70 nanometer to 900 nanometers. The particle size distribution of the nanoresin particles may be considered as the particle size distribution obtained after the suspension has been subjected to 5 pulses of frequency of 33±3 KHz with intervals of 1 minute each, as described above.

The individual drug loaded nano-resin particles have a particle size distribution such that value of $D_{90}$ is 70 nanometer to 900 nanometer (nm or nms), preferably 200 nms to 700 nms. Further wherein, such drug-loaded nanoresin particles have a mean particle size ($D_{50}$) of less than 500 nms.

Preferably, the $D_{50}$ value is 50 nanometers to 350 nanometers. The particle size distribution of the nanoresin may be further characterized in that the $D_{10}$ is less than 300 nms, preferably 10 nms to 250 nms.

According to the present invention, the reversible clusters have a particle size distribution such than mean size is at least 2 micrometer (µm or microns). In preferred embodiments, the particle size distribution is such than the $D_{90}$ is less than 80 micrometers, preferably less than 50 micrometers, most preferably less than 30 micrometers. The particle size distribution may be further characterized in than the $D_{50}$ is less than 40 micrometers, preferably less than 20 micrometers, more preferably less than 10 micrometers. The reversible clusters, upon application of shear deagglomerate or deaggregate to form drug loaded nanoresin particles.

The present invention provides an aqueous suspension comprising (a) reversible clusters of drug loaded nano-resin particles, said clusters have a $D_{50}$ value of at least 2 micrometers and said drug loaded nano-resin particles have a particle size distribution characterized in that the $D_{90}$ value is 70 nanometers to 900 nanometers, (b) a suspending agent.

The present invention was found to be increasing the bioavailability and/or prolonging ophthalmic action of a drug, when instilling into the eye, the aqueous suspension of reversible clusters of drug loaded nano-resin particles, said clusters having a $D_{50}$ value of at least 2 micrometers and said drug loaded nano-resin particles having a particle size distribution characterized in that the $D_{90}$ value is 70 nanometers to 900 nanometers, wherein the aqueous suspension contains a suspending agent. The present invention also provides a method of increasing the bioavailability and/or prolonging ophthalmic action of a drug, said method comprising instilling into the eye an aqueous suspension comprising (a) reversible clusters of drug loaded nano-resin particles, said clusters having a $D_{50}$ value of at least 2 micrometers and said drug loaded nano-resin particles having a particle size distribution characterized in that the $D_{90}$ value is 70 nanometers to 900 nanometers, and (b) a suspending agent.

The present invention also provides a method of increasing the bioavailability and/or prolonging ophthalmic action of a drug, the method comprising providing an aqueous suspension comprising (a) reversible clusters of drug loaded nano-resin particles, said clusters having a $D_{50}$ value of at least 2 micrometers and said drug loaded nano-resin particles having a particle size distribution characterized in that the $D_{90}$ value is 70 nanometers to 900 nanometers, and (b) a suspending agent.

The 'drugs' suitable according to the method of the present invention include therapeutically active ingredients that are capable of forming a salt with an acid or an alkali, and includes ionizable therapeutically active ingredients. According to one aspect, drugs include ionizable drugs that can form salts with acids, known as cationic drugs. According to another aspect, drugs include ionizable drugs that can form a salt with a base or an alkali, known as anionic drugs. Non limiting examples of the drugs according to the present invention include drugs that are used ophthalmically such as but not limited to antiglaucoma agents; antibiotics or anti-infective agents; anti-allergic agents; anti-inflammatory/anti-allergic steroids; non-steroidal anti-inflammatory agents; decongestant; local anaesthetic agents; mydriatic agents. The antiglaucoma agents include group of drugs such as beta-blockers, carbonic anhydrase inhibitors, alpha-adrenergic agonists, prostaglandins, parasympathomimetics and cholinesterase inhibitors. Non-limiting examples of prostaglandins that may be used include, latanoprost, travoprost, bimatoprost, tafluprost, isopropyl unoprostone, 8-iso-prostaglandin-E2, and the like and pharmaceutically acceptable salts thereof; Non-limiting examples of beta-blockers that may be used include, timolol, levobunolol, befundol, metipranolol, carteolol, betaxolol, levobetaxolol, befunolol, labetalol, propranolol, metaprolol, bunalol, esmalol, pindolol, hepunolol, metipranolol, celiprolol, azotinolol, diacetolol, acebutolol, atenolol, isoxaprolol or pharmaceutically acceptable salts thereof; Non-limiting examples of carbonic anhydrase inhibitors that may be used include, brinzolamide, dorzolamide, acetazolamide, methazolamide, dichlorophenamide and the like and pharmaceutically acceptable salts thereof; Non-limiting examples of alpha-adrenergic agonists that may be used include, brimonidine, dipivefrine, clonidine, and clonidine derivatives—p-aminoclonidine, p-acetoamidoclonidine, apraclonidine and the like and pharmaceutically acceptable salts thereof; Non-limiting examples of cholinesterase inhibitors that may be used include, physostigmine, ecothiopate and the like and pharmaceutically acceptable salts thereof; Non-limiting examples of parasympathomimetics that may be used include pilocarpine, demecarium and the like and pharmaceutically acceptable salts thereof. Non-limiting examples of antibiotics or anti-infective agents includes moxifloxacin, besifloxacin, gentamicin, neomycin; erythromycin, ciprofloxacin, polymyxin B, beta-lactam antibiotics, tetracycline, chlortetracycline and the like and pharmaceutically acceptable salts thereof; Anti-allergic agents includes olopatadine emedastine, azelastine, epinastine, levocabastine, bepotastine, pheniramine, chlorpheniramine, epinephrine, proepinephrine, norepinephrine, pyrilamine and the like and pharmaceutically acceptable salts thereof; Anti-inflammatory/anti-allergic steroids includes dextromethorphan, dexamethasone, prednisolone and the like and pharmaceutically acceptable salts thereof. Non-steroidal anti-inflammatory agents includes ketotifen and the like and pharmaceutically acceptable salts thereof; Decongestant includes oxymetazoline, phenylephrine, naphazoline, antazoline and the like and pharmaceutically acceptable salts thereof; Local anaesthetic agents includes proparacaine, lidocaine and the like and pharmaceutically acceptable salts thereof; Mydriatic agents includes cyclopentolate and the like and pharmaceutically acceptable salts thereof. A combination of two or more drugs may be used. Other drugs which are anionic drugs includes diclofenac, bromfenac, sulfacetamide, flurbiprofen, ketorolac, lodoxamide, sulfacetamide, cromolyn, pemirolast or their pharmaceutically acceptable salts or mixtures thereof. According to preferred aspect, the drug is selected from brimonidine, doxycycline, bromfenac, olopatadine, emedastine, dorzolamide, ciprofloxacin, moxifloxacin, besifloxacin, gentamicin, neomycin, polymyxin B, ketotifen, phenylephrine, pyrilamine, dipivefrin, oxymetazoline, levocabastine, azelastine, epinastine, bepotastine, dipivefrin, naphazoline, apraclonidine, levobunolol, betaxolol, levobetaxolol, timolol, carteolol, dextromethorphan, cyclopentolate, proparacaine, pilocarpine, diclofenac, sulfacetamide, flurbiprofen, ketorolac or their pharmaceutically acceptable salts or mixtures thereof.

According to one preferred embodiment, drug is brimonidine or its pharmaceutically acceptable salt thereof. According to more preferred embodiment, drug is brimonidine tartarate. Brimonidine tartrate is chemically known as 5-bromo-6-(2-imidazolidinylideneamino) quinoxaline L-tartrate. Brimonidine is an alpha adrenergic agonist that reduces the elevated intraocular pressure (IOP) of the eye associated with glaucoma. Brimonidine or its pharmaceutically acceptable salt is present in the aqueous suspension of the present invention in therapeutically active amounts. In preferred embodiments, brimonidine or its pharmaceutically acceptable salt is present at a concentration of 0.05% to 0.5% weight by volume. In one specific embodiment, brimonidine tartrate is present at a concentration of 0.35% weight by volume. In another embodiment, the aqueous suspension of the present invention contains brimonidine tartrate at a concentration of 0.15% weight by volume.

According to one aspect of the invention, the resin is an ion exchange resin. The ion exchange resins are covalently bound in repeating positions on the resin chain. These charged groups associate with other ions of opposite charge. Depending on whether the mobile counterion is a cation or an anion, it is possible to distinguish between cationic and anionic exchange resins. The matrix in cationic exchangers carries ionic groups such as sulfonic, carboxylate and phosphate groups. The matrix in anionic exchangers carries primary, secondary, tertiary or quaternary ammonium groups. The resin matrix determines its physical properties, its behavior towards biological substances, and to a certain extent, its capacity. Since cationic drugs such as brimonidine have a positive charge, they can bind with cation exchange resins. Sulfonic acid exchangers are the most common cation exchange resins used for drug resinate aqueous suspension of the present invention. In general, they are cross-linked polystyrenes with sulfonic acid groups which have been introduced after polymerization by treatment with sulfuric acid or chlorosulfonic acid. Suitable cation exchange resins that may be used in the present invention includes, but are not limited to, sodium polystyrene divinyl benzene sulphonate, such as marketed by Rohm and Haas, under the trade name Amberlite™ IRP 69; polacrilex resin which is derived from a porous copolymer of methacrylic acid and divinylbenzene, such as marketed by Rohm and Haas, under the trade name Amberlite™ IRP 64; polacrilin potassium, which is a potassium salt of a cross linked polymer derived from methacrylic acid and divinylbenzene, such as marketed by Rohm and Haas, under the trade name Amberlite™ IRP 88. The resins marketed by the company Ion Exchange India Ltd., under the tradenames such as INDION™ 234; INDION™ 264; INDION™ 204; INDION™ 214 may also be used. In one embodiment, the preferred resin used in the present invention is Amberlite IRP69 which is derived from a sulfonated copolymer of styrene and divinyl benzene. Amberlite IRP-69 is a pharmaceutical grade strong cation exchange resin and structurally a polystyrene sulfonic acid resin cross-linked with divinyl benzene, i.e. polystyrene divinyl benzene sulfonate.

Amberlite IRP-69 resin is available commercially from Rhom & Haas Company. The mobile or exchangeable cation in the resin is sodium, which can be exchanged for, or replaced by, cationic (basic) species. In embodiments of the ion exchange delivery system of the present invention, positively charged cationic drug is bound to the negatively charged sulfonic acid groups of the Amberlite resin.

Suitably, in some embodiments of the present invention, the ion-exchange resin is an anion exchange resin and the drug is anionic in nature. Non-limiting example of anionic ionizable drugs include diclofenac, bromfenac, sulfacetamide, flurbiprofen, lodoxamide, sulfacetamide, cromolyn, pemirolast, ketorolac or their pharmaceutically acceptable salts or mixtures thereof. The matrix in anionic exchange resin generally carries primary, secondary, tertiary or quaternary ammonium groups. Suitable anion exchange resins that may be used in the present invention includes, but are not limited to, cholestyramine resin, such as marketed by Rohm and Haas, under the trade name Duolite™ AP143/1093; INDION™ 860, which is a macroporous weakly basic anion resin having a tertiary amine functionality attached to a polymeric styrene divinyl benzene matrix; INDION™GS400, which is strong base Type II anion exchange resin, based on cross linked polystyrene matrix with benzyl dimethyl ethanol amine functional groups.

The amount of ion exchange resin present in the aqueous suspension of the present invention, may range from about 0.05% to 5.0% weight by volume of the suspension. The weight ratio of resin to drug may range from 0.1:1 to 1:0.1, more preferably from 0.3:1 to 1:0.3. In one preferred embodiment, the weight ratio between the nano-resin particles and drug is about 1:1. Nanoresin particles used according to the present invention have a particle size distribution characterized in that the $D_{90}$ value is 70 nms to 900 nms, preferably 200 nms to 700 nms.

The aqueous suspension may contain one or more suspending agents. The suspending agents are used to increase the viscosity of the suspension, to cause clustering of the nanoresin particles into micron size clusters, and to prevent the caking of the suspension. The suitable suspending agent is selected from an anionic polymer, a non-ionic polymer or mixtures thereof. The anionic polymers may be selected from the group consisting of polymers of acrylic acid like carboxyvinyl polymer or carbomer, also known as Carbopols. Various grades of carbomers including Carbopol 934P, 974, 1342 and the like may be used in the present invention. The polymers of acrylic acid may be present in the aqueous suspension of the present invention in an amount ranging from about 0.01% to 0.5% weight by volume of the suspension. Other anionic polymers that can be used include, but are not limited to, sodium hyaluronate; sodium carboxymethylcellulose; guargum; chondroitin sulphate; sodium alginate. Particularly, the preferred anionic polymers that may be used include Carbopol 974P. This anionic polymer is most preferably used in an amount of 0.1% w/v of the suspension. The non-ionic polymers that can be used according to the present invention may be selected from the group consisting of non-ionic polymers such as polyvinyl pyrrolidone, soluplus-a polyvinyl caprolacatam-polyvinyl acetate-PEG graft co-polymer, poloxamers, polyvinyl alcohol, polypropylene glycol, cellulose derivatives like hydroxyethylcellulose, hydroxypropyl cellulose, hydroxypropyl methylcellulose, methyl cellulose, ethyl cellulose and the like. The non-ionic polymers may be present in the aqueous suspension of the present invention in an amount ranging from about 0.1% to about 5.0% weight by volume of the suspension. The preferred non-ionic polymers that may be used include hydroxypropyl methylcellulose and polyvinylpyrrolidone. Various pharmaceutically acceptable grades of hydroxypropyl methylcellulose (also known as hypromellose or HPMC or Methocel) and polyvinylpyrrolidine (also known as povidone or PVP or plasdone) may be used. The preferred grades of polyvinylpyrrolidine which can be used in the suspensions of the present invention include PVP K-30, PVP K-25, PVP K-50; PVP K-60 and PVP K-90. It may be present in the aqueous suspension in an amount ranging from about 0.5% to about 3.0% weight by volume of the suspension. The most preferred grade used in the aqueous suspension of the present invention is PVP K-90, whose 10% w/v aqueous solution has a dynamic viscosity in the range of about 300.0 cps to about 700.0 cps at 20° C., and has an approximate molecular weight of about 1,000,000 to 1,500,000. In preferred embodiment, polyvinylpyrrolidine PVP K-90 is used in an amount of 1.2% w/v of the suspension. The preferred grades of hydroxypropylmethylcellulose which may be selected to be used in the aqueous suspensions of the present invention include, but is not limited to METHOCEL E, (USP grade 2910/HYPROMELLOSE 2910); METHOCEL F, (USP grade 2906/HYPROMELLOSE 2906); METHOCEL A15 (Premium LV); METHOCEL A4C (Premium); METHOCEL A15C (Premium); METHOCEL A4M (Premium), HPMC USP Grade 1828 and the like. It may be present in the aqueous suspension of the present invention in an amount ranging from about 0.5% to about 3.0% weight by volume of the suspension. In most preferred embodiment, the aqueous suspension comprises Hypromellose 2910 in an amount of 0.3% w/v. As auxiliary to the suspending agents the flocculation of nanoresin particles may also be assisted by electrolytes.

The aqueous suspensions according to the present invention may have a viscosity ranging from about 2 cps to 2000 cps, preferably about 5 cps to 400 cps. The viscosity of the aqueous suspensions may be measured by known techniques and instruments such as by Brookfield viscometer, under standard conditions. It is to be noted that the aqueous suspensions according to one embodiment of the present invention, maintains its viscosity upon instillation into the eye, i.e. the viscosity do not change substantially upon coming in contact with the eye fluid that contains various ions such as sodium, potassium, calcium, magnesium, zinc, chloride, and bicarbonate.

The aqueous suspensions according to the present invention may additionally comprise other pharmaceutically acceptable excipients such as chelating agents, preservatives and adjuvants for preservatives. The aqueous suspension may further include one or more osmotic agents/tonicity adjusting agents, one or more pharmaceutically acceptable buffering agents and/or pH-adjusting agents. These excipients may be dissolved or dispersed in a pharmaceutically acceptable aqueous vehicle such as water for injection.

In order to achieve, and subsequently maintain, an optimum pH suitable for ophthalmic preparations, the aqueous suspensions of the present invention essentially contains a pH adjusting agent and/or a buffering agent in suitable amounts. The preferred range of pH for the aqueous suspension is about 5.0 to about 8.0, preferably 7.0 to 8.0. The most preferred pH is about 7.4. The aqueous suspensions of the present invention comprise a pharmaceutically acceptable pH adjusting agent that may be selected from the group comprising tromethamine, acetic acid or salts thereof, boric acid or salts thereof, phosphoric acid or salts thereof, citric acid or salts thereof, tartaric acid or salts thereof, sodium hydroxide, potassium hydroxide, sodium carbonate, sodium hydrogen carbonate, trometamol, and the like and mixtures thereof. Particularly, preferred pH adjusting agents that may be used in the aqueous suspensions of the present invention include tromethamine, acetic acid, hydrochloric acid, sodium carbonate and sodium hydroxide, most preferably tromethamine.

The aqueous suspensions of the present invention are required to be isotonic with respect to the ophthalmic fluids present in the human eye and are characterized by osmolalities of 250-375 mOsm/kg. Osmolality is adjusted by addition of an osmotic/tonicity adjusting agent. Osmotic agents that may be used in the suspension of the present invention to make it isotonic with respect to the ophthalmic fluids present in the human eye, are selected from the group comprising sodium chloride, potassium chloride, calcium chloride, sodium bromide, mannitol, glycerol, sorbitol, propylene glycol, dextrose, sucrose, and the like, and mixtures thereof. These are used in suitable amounts to maintain desired osmolarity. In preferred embodiments of the present invention, a non-ionic osmotic agent such as mannitol is used as the osmotic agent. Mannitol may be present in the suspension of the present invention in an amount ranging from about 2.0% to about 6.0% w/v, preferably from about 3.0% to about 5.0% w/v and most preferably in an amount of about 4.5% w/v.

Further, the aqueous suspensions of the present invention may comprise preservatives in antimicrobial effective amounts. The preservative that may be used in the aqueous suspensions of the present invention may be selected from, but not limited to: quaternary ammonium compounds such as benzalkonium chloride (BKC), benzododecinium bromide, cetrimonium chloride, polixetonium and benzethonium chloride; organic mercurials such as phenylmercuric acetate, phenylmercuric nitrate and thimerosal; parabens such as methyl and propyl paraben; ethyl paraoxybenzoate or butyl paraoxybenzoate; acids and their pharmaceutically acceptable salts such as sorbic acid, potassium sorbate, ascorbic acid, boric acid, borax, salicylic acid; substituted alcohols and phenols such as chlorobutanol, benzyl alcohol, phenyl ethanol; amides such as acetamide; other preservatives like Polyquad®, polyhexamethylene biguanide, sodium perborate, aminomethyl propanol, chlorhexidine acetate, self preserved system containing ionic preservative like combination of zinc and borate; and the like, and combinations thereof. Preferably the ophthalmic aqueous suspensions of the present invention comprise 'quaternary ammonium compound' as a preservative, particularly benzalkonium chloride. Benzalkonium chloride is characterized as a mixture of alkyldimethylbenzylammonium chlorides. It is employed in the aqueous suspension of the present invention in a concentration of about 0.005 to about 0.05% w/v, preferably 0.02% w/v. The aqueous suspensions may further comprise an adjuvant to a preservative in suitable amounts, such as N-lauroyl sarcosine sodium. Suitable chelating agent that may be used is edetate disodium.

The aqueous suspension of the present invention remains physically and chemically stable during the shelf life of the product. For instance, in case of aqueous suspensions containing the drug brimonidine, there occurs no significant change in assay of brimonidine after long term storage of the suspension. The assay of the drug remained within specified limit and no degradation products or impurities were observed upon storage. Also, there was no significant increase in related substances.

It was found from the tissue distribution study that the method according to the present invention is capable of delivering a drug to the posterior segment of the eye. The ability of the present invention to deliver the drug in the posterior segment of the eye make it suitable for treating diseases of the posterior segment, which are difficult to treat. For instance in case of brimonidine, delivery to posterior segment, helps in preventing degeneration of neurons and imparting neuroprotection action. This was an indeed a surprising finding because the method provided not only increased bioavailability of drugs along with prolonged ophthalmic action, upon instillation into the eye, but also could achieve delivery to the posterior segment. Without wishing to be bound by any theory, it is believed that the reversible cluster of the drug loaded nano-resin particles upon instillation into the eye, declusters under shear due to eye blinking. The declustered individual drug-loaded nano-resin particles spread on the surface of the cornea and subsequently releases the drug through ion exchange phenomenon under the effect of ions present in the ocular tissue. There occurs decrease in naso-lacrymal drainage of the drug. The overall phenomenon causes increased bioavailability of the drug along with prolonged ophthalmic action.

In preferred embodiments, the present invention provides a method of increasing the bioavailability and/or prolonging the ophthalmic action of a drug, the method comprising instilling into the eye an aqueous suspension comprising reversible clusters of drug loaded nano-resin particles, said clusters have a $D_{50}$ value of at least 2 micrometers and said drug loaded nano-resin particles have a particle size distribution characterized in that the $D_{90}$ value is 70 nanometers to 900 nanometers, wherein the nano-resin is selected from a cation exchange or an anion exchange resin, wherein the aqueous suspension further comprises a suspending agent selected from a non-ionic polymer, an anionic polymer or mixtures thereof.

In preferred embodiments, the present invention provides a method of increasing the bioavailability and/or prolonging the ophthalmic action of a drug, the method comprising instilling into the eye an aqueous suspension comprising reversible clusters of drug loaded nano-resin particles, said clusters having a $D_{50}$ value of at least 2 micrometers and said drug loaded nano-resin particles having a particle size distribution characterized in that the $D_{90}$ value is 70 nanometers to 900 nanometers, wherein the nano-resin is selected from a cation exchange or an anion exchange resin, wherein the aqueous suspension further comprises a suspending agent selected from a non-ionic polymer, an anionic polymer or mixtures thereof, and wherein the drug is brimonidine tartarate. Brimonidine tartarate is present at a concentration ranging from about 0.05% w/v to 0.5% w/v of the aqueous suspension. The weight ratio between the nano-resin particles and brimonidine may range from about 0.1:10 to 10:0.1, preferably from 0.1:1 to 1:0.1, more preferably 0.3:1 to 1:0.3. In one preferred embodiment, the weight ratio between the nano-resin particles and brimonidine is about 1:1. In one specific embodiment, the ion exchange resin is polystyrene divinyl benzene sulfonate and it is present at a concentration ranging from about 0.05% w/v to 0.5% w/v of the aqueous suspension.

In a more particularly preferred embodiment, the present invention provides an aqueous suspension comprising (a) reversible clusters of drug loaded nano-resin particles, said clusters having a $D_{50}$ value of at least 2 micrometers and said drug loaded nano-resin particles having a particle size distribution characterized in that the $D_{90}$ value is 70 nanometers to 900 nanometers, and (b) a suspending agent; wherein the drug is brimonidine tartarate and it is present in an amount of 0.35% w/v; resin is polystyrene divinyl benzene sulfonate; suspending agent is a mixture of carbopol, polyvinylpyrrolidone and hydroxypropylmethyl cellulose. The weight ratio between the nano-resin particles and brimonidine is about 1:1; and pH is about 7 to 8. Further, surprisingly, the aqueous suspension of the present invention in spite of containing higher concentration (about 0.35% w/v) of the drug, provided a ophthalmic suspension that was very safe with no adverse effects or toxicity. This result was indeed surprising because inspite of instilling the aqueous suspension for consecutive 14-day in New Zealand white rabbits, no adverse effects were observed. The results also provided unexpected finding that even at an ocular dosing as high as six times of the desired dose, there was no adverse effects in the eye such as local toxicity at the site of application or systemic toxicity. Further, there were no signs of irritation, swelling or redness, or allergic reactions.

According to this aspect, the aqueous suspension of the present invention was found to increase the bioavailability as well as prolonging ophthalmic action of brimonidine tartrate at a concentration of 0.35% weight by volume when instilled into the eye once-a-day. This provided an effective use in the treatment of glaucoma by once-a-day instillation of the aqueous suspension into the eyes. The method of increasing the bioavailability and/or prolonging ophthalmic action according to this embodiment was found to provide equivalent efficacy to that of Alphaghan P®, but at a reduced frequency of administration that is, once daily instillation as compared to thrice daily instillation as prescribed for Alphagan P®. (illustrated in Example 8 of the specification). The method of the invention also advantageously provide optimum efficacy at a reduced dose. For instance, in this embodiment, a reduced (lower) daily dose is administered in case of once daily administration of 0.35% w/v suspension of the present invention as compared to thrice daily administration of 0.15% w/v formulation of Alphagan P®, but still equivalent efficacy is obtained.

In another preferred embodiment, the present invention provides an aqueous suspension comprising (a) reversible clusters of drug loaded nano-resin particles having a particle size distribution characterized in that the $D_{90}$ value is 70 nanometers to 900 nanometers, said clusters having a mean size ($D_{50}$ value) of at least 2 micrometers, and (b) a suspending agent wherein the drug is brimonidine tartrate and it is present in an amount of 0.15% w/v; resin is polystyrene divinyl benzene sulfonate; suspending agent is a mixture of carbopol, polyvinylpyrrolidone and hydroxypropylmethyl cellulose. The weight ratio between the nano-resin particles and brimonidine is about 1:1; and pH is about 7 to 8. The aqueous suspension when instilled twice a day was found to provide equivalent efficacy to that of Alphaghan P®, which is instilled thrice a day. This has been established and provided in Example 9 of the patent specification. According to this aspect, the present invention thus provides a method of increasing the bioavailability and/or prolonging ophthalmic action of the drug, comprising providing the aqueous suspension described above. The method of the invention advantageously provide optimum efficacy at a reduced daily dose. For instance, in this embodiment, a reduced (lower) daily dose is administered in case of twice daily administration of 0.15% w/v suspension of the present invention as compared to thrice daily administration of 0.15% w/v formulation of Alphagan P®, but still equivalent efficacy is obtained.

According to one particular embodiment, the aqueous suspension of the present invention comprises an ionizable antiglaucoma drug for example brimonidine and an additional antiglaucoma drug selected from the group consisting of beta-blockers, carbonic anhydrase inhibitors, alpha-adrenergic agonists, prostaglandins, parasympathomimetics and cholinesterase inhibitors. Non-limiting examples of prostaglandins that may be used include, latanoprost, travoprost, bimatoprost, tafluprost, isopropyl unoprostone, 8-iso-prostaglandin-E2, or salts thereof. Non-limiting examples of beta-blockers that may be used include, timolol, levobunolol, befundol, metipranolol, carteolol or salts thereof. Non-limiting examples of carbonic anhydrase inhibitors that may be used include, brinzolamide, dorzolamide, acetazolamide, methazolamide, dichlorophenamide or salts thereof. Non-limiting examples of alpha-adrenergic agonists that may be used include, brimonidine, apraclonidine, dipivefrine. Non-limiting examples of cholinesterase inhibitors that may be used include, physostigmine, ecothiopate. In practice, the anti-glaucoma drug forms between 0.1% and 1.0% by weight of the composition.

In one preferred embodiment, the aqueous suspension of the present invention comprises a combination of ionizable antiglaucoma drugs brimonidine and timolol or their salts. In this embodiment, the aqueous suspension comprises brimonidine tartrate and timolol maleate in therapeutically effective amounts suitable for reducing the elevated intraocular pressure and treating glaucoma. In one specific embodiment, the aqueous suspension of the present invention comprise brimonidine tartrate in an amount ranging from 0.2% w/v to 0.35% w/v and timolol maleate in an amount of 0.1 to 0.5% w/v, wherein the suspension is suitable to provide desired therapeutic efficacy by once-a-day topical instillation to the eye. In another specific embodiment, the aqueous suspension of the present invention comprise brimonidine tartrate in an amount of about 0.1% w/v and timolol maleate in an amount of about 0.5% w/v and wherein the suspension is suitable to provide desired therapeutic efficacy by twice-a-day topical instillation to the eye.

In another preferred embodiment, the present invention provides a method of increasing the bioavailability and/or prolonging ophthalmic action of a drug, the method comprising instilling into the eye an aqueous suspension comprising reversible clusters of drug loaded nano-resin particles, said clusters having a mean size of at least 2 micrometers, said drug loaded nano-resin particles having a particle size distribution characterized in that the $D_{90}$ value is 70 nanometer to less than 900 nanometers, wherein the drug is bromfenac sodium; and the nano-resin is an anion exchange resin, preferably Indion™ 860. According to this aspect, the present invention also provides a method of prolonging ophthalmic action of bromfenac sodium, comprising administering to the eyes, the aqueous suspension described above.

In another preferred embodiment, the present invention provides a method of increasing the bioavailability and/or prolonging ophthalmic action of a drug, the method comprising instilling into the eye an aqueous suspension comprising reversible clusters of drug loaded nano-resin particles, said clusters having a mean size of at least 2 micrometers, said nano-resin particles having a particle size distribution characterized in that the $D_{90}$ value is 70 nanometer to less than 900 nanometers, wherein the drug is doxycycline hyclate; and the nano-resin is an cation exchange resin, preferably sodium polystyrene divinyl benzene sulfonate.

While the present invention is disclosed generally above, additional aspects are further discussed and illustrated with reference to the examples below. However, the examples are presented merely to illustrate the invention and should not be considered as limitations thereto.

Comparative Example 1

The resin 'Amberlite® IRP 69' was washed with absolute alcohol multiple times. The resin was further washed with Millipore water until a pH close to neutral (pH 7.0) was attained. The particle size distribution of the resin was measured using Malvern Mastersizer 2000 Ver.5.60, Malvern Instruments Ltd., Malvern, UK. The histogram of the resin is depicted in FIG. 1. The resin has particle size distribution such that $D_{10}$ is 2.341 micron, $D_{50}$ is 5.175 micron and $D_{90}$ is 10.41 micron. The resin was used for preparation of the composition of Table 1.

TABLE 1

Aqueous suspension of cationic drug: Brimonidine Tartrate with Amberlite resin IRP69 of average particle size of 5 microns

| S. No. | Ingredients | Amount (% w/v) |
|---|---|---|
| 1 | Brimonidine Tartrate | 0.35 |
| 2 | Amberlite IRP 69 | 0.35 |
| 3 | Hydroxy propyl methyl cellulose | 0.3 |
| 4 | Polyvinylpyrrolidone | 1.2 |
| 5 | Carbopol 974P (carbomer) | 0.1 |
| 6 | Benzalkonium Chloride | 0.02 |
| 7 | Edetate Disodium | 0.1 |
| 8 | N-Lauroylsarcosine sodium | 0.06 |
| 9 | Mannitol | 4.5 |
| 10 | Tromethamine q.s to adjust pH to 7.4 | 0.32 |
| 11 | Water for Injection | q.s. |

In a stainless steel (SS 316) beaker, 15% water for injection of total batch size was taken and heated to 85° C. Hydroxy propyl methyl cellulose (hypromellose 2910) was dispersed with high speed stirring to obtain uniform dispersion. The stirring was continued till temperature reached 25° C. In another stainless steel (SS 316) beaker, a portion of water for injection of total batch size was taken at 25° C. Polyvinylpyrrolidone (povidone K-90) was dispersed in water for injection with stirring to obtain uniform dispersion.

In a stainless steel (SS 316) beaker, about 10% water for injection of total batch size was taken and heated at 65° C. Carbopol 974P was dispersed in heated water for injection with stirring. The stirring was continued till the temperature reached 25° C. The Carbopol 974P slurry was neutralized (pH7.4) with tromethamine. The hypromellose and povidone polymer dispersions obtained above were added sequentially to the carbopol 974P phase. The polymer mixture was autoclaved at 121° C. for 20 minutes. N-lauryl sarcosine sodium was mixed in a portion of water for injection of total batch size and added to the polymer phase after filtration through 0.2 micron nylon filter. Mannitol was dissolved in a portion of water for injection at 50-60° C. and benzalkonium chloride, and edetate disodium were added to form a clear solution. This solution was added to the above polymer phase. 15% water for injection of total batch size was taken in a vessel and Amberlite IRP 69 was dispersed with stirring. In another vessel, 15% water for injection of total batch size was taken and brimonidine tartrate was added with stirring to dissolve. This solution was filtered through 0.2 micron and 0.45 micron nylon filter. Filtered brimonidine tartrate solution was added to above autoclaved amberlite IRP 69 dispersion and stirred for 30 minutes. The Amberlite IRP 69 & Brimonidine tartrate dispersion was added to the polymer mixture obtained above with stirring and stirring was continued for 1 hr. The pH was adjusted with tromethamine solution to about 7.4. The volume of suspension was finally made up to 100% batch size. The suspension was stirred for 60 minutes, followed by homogenization at 15000 rpm for 10 mins.

Figure 2:
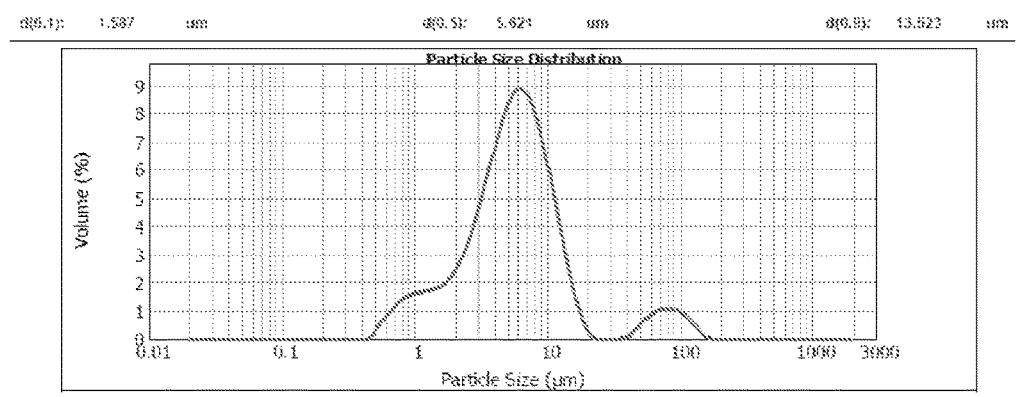
FIGS. 2-7 are illustrative histograms for particle size distribution of the drug loaded resin particles in the suspension prepared according to Comparative Example 1, upon application of shear by subjecting to sonication and measuring particle size distribution after one, two, three, four and five minutes, respectively. The histograms reveal that there is no change in the particle size upon application of shear.

The suspension was subjected to sonication at a frequency of of 33±3 KHz, for 5 seconds and a sample was withdrawn to measure the particle size distribution by Malvern Mastersizer 2000, Ver.5.60, Malvern Instruments Ltd., Malvern, UK. The histograms of the particle size distribution upon application of first pulse of shear/sonication for 5 seconds is depicted by FIG. 2. Following intervals of one minute each, the sonication process and subsequent measurement of the particle size was repeated till 5 minutes. FIGS. 3 to 7, are the histograms of the particle size distribution at the end of each minute, till 5 minutes, respectively. See table number 2 for the particle size distribution.

TABLE 2

Effect of shear on the particle size distribution of the resin particles in the suspension

Figure 3:
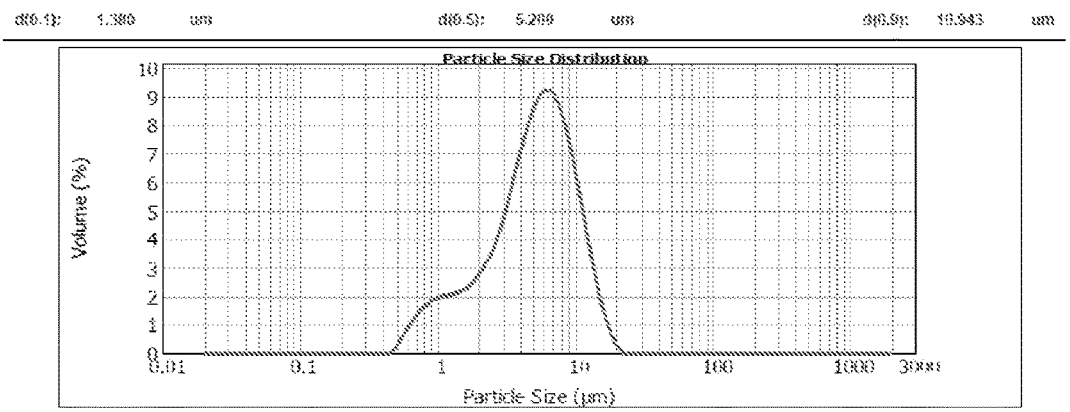
Figure 4:
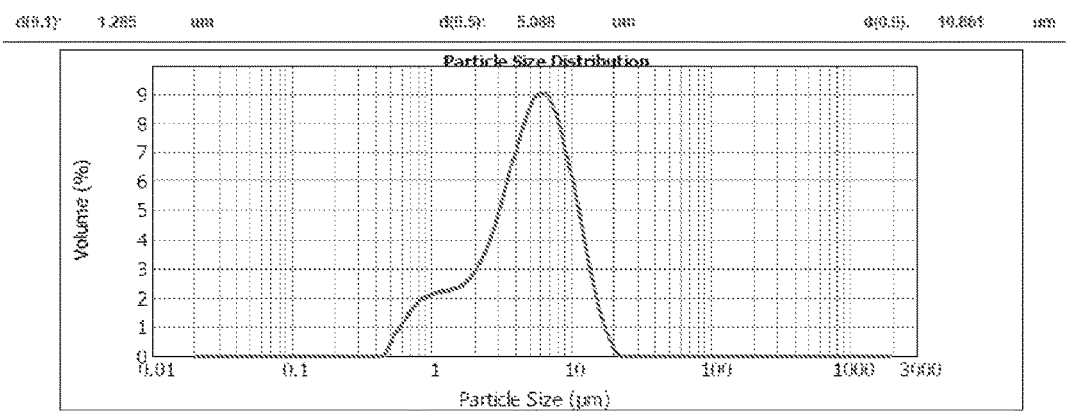
Figure 5:
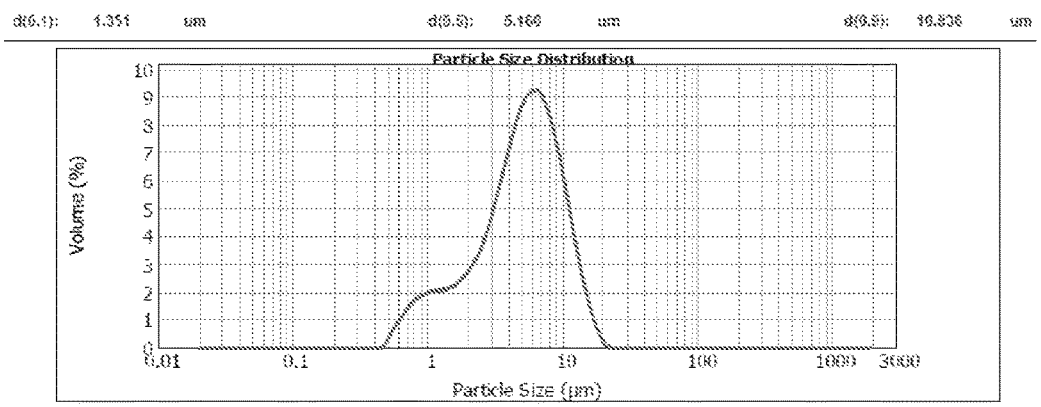
Figure 6:
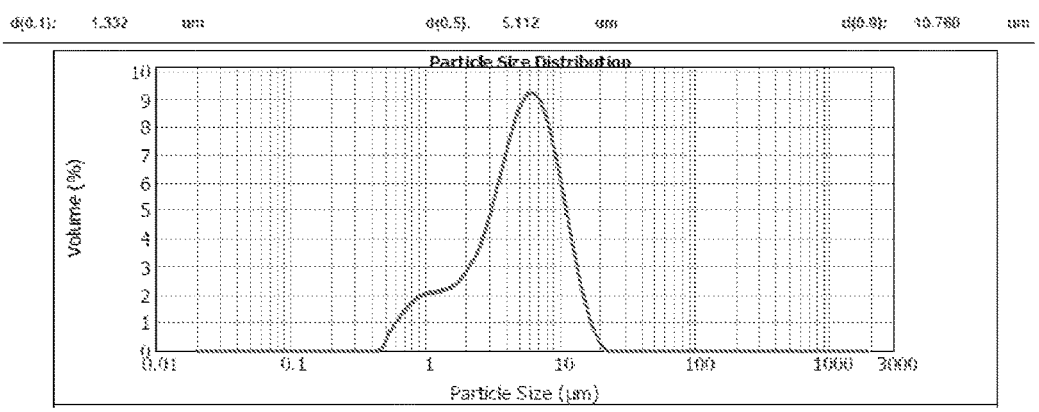
Figure 7:
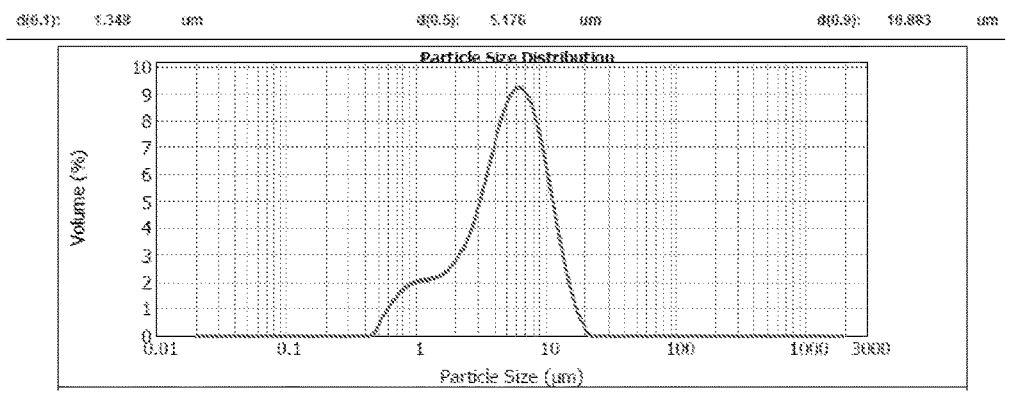

| | | Volume mean diameter in microns recorded by Malvern lazer diffraction method | | | | | |
|---|---|---|---|---|---|---|---|
| | | Initial | 1 min | 2 min | 3 min | 4 min | 5 min |
| | | | | FIG. No. | | | |
| Example No. | PSD* | FIG. 2 | FIG. 3 | FIG. 4 | FIG. 5 | FIG. 6 | FIG. 7 |
| Comparative example 1 | $D_{10}$ | 1.587 | 1.380 | 1.285 | 1.351 | 1.332 | 1.348 |
| | $D_{50}$ | 5.621 | 5.200 | 5.088 | 5.160 | 5.112 | 5.176 |
| | $D_{90}$ | 13.523 | 10.943 | 10.861 | 10.836 | 10.760 | 10.883 |

PSD*—Particle Size Distribution in Volume mean diameter in microns

Observation: It was observed that particle size distribution of the drug loaded resin particles remains in the microns size, in that the $D_{50}$ was 5 microns at the end of 5 minutes, after application of shear by sonication at a frequency of 33±3 KHz, for 5 seconds. Further, the $D_{90}$ was also not affected by the shear force, and remained in the range of 10 microns.

Example 1

Preparation of purified nanoresin: The resin 'Amberlite® IRP69' was washed multiple times with a suitable alcohol such as methanol or absolute alcohol. The resin was further washed with heated Millipore water until a pH close to neutral (pH 7.0) was attained. The washed resin was subjected to wet milling to reduce particle size to nanometer range, having $D_{90}$ less than 900 nms. The washed resin and stabilized Zirconia beads were added to water for injection in a vessel containing a teflon coated magnetic bead. The vessel was kept for wet grinding on a magnetic stirrer for about 24-48h to obtain nano size milled resin particles. The slurry so formed was passed through a 25 micron sieve to remove beads and further passed through 40 micron PP filter. The milled resin suspension obtained above was subjected to diafiltration using a 500 kD hollow fiber cartridge wherein the water extractable impurities were reduced to less than 1.0% by weight of resin. The milled resin suspension was further washed with water for injection. This slurry was lyophilized to get the dried powder form of the milled purified resin.

Figure 8:
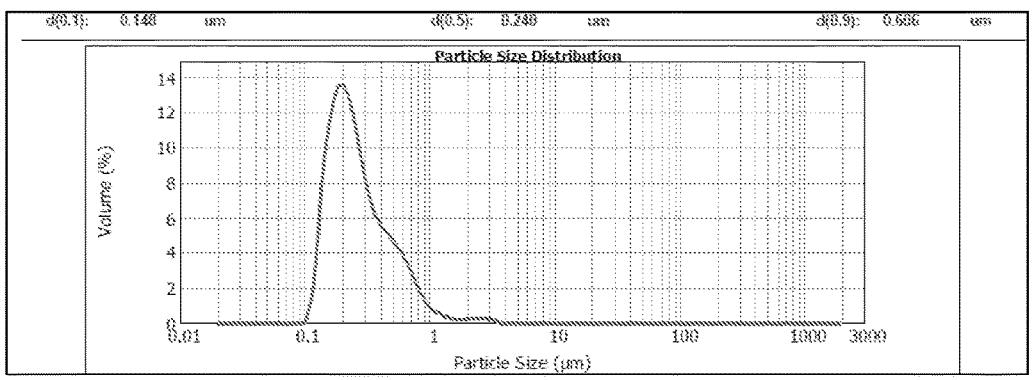
FIG. 8 is an illustrative histogram for the nano-resin particles used in the preparation of aqueous suspension of the present invention.

The particle size distribution of the milled resin was measured using Malvern Mastersizer 2000 Ver.5.60, Malvern Instruments Ltd., Malvern, UK. The histogram of the resin is depicted in FIG. 8. The particle size distribution was such that $D_{10}$=0.148 microns, $D_{50}$=0.24 microns and $D_{90}$=0.606 microns. The nanoresin was used for the preparation of aqueous suspension in Example 2 to Example 5.

Example 2 (A) and 2 (B)

TABLE 3

Details of the aqueous suspension of the present invention

| | Ingredients | Amounts- % w/v | |
|---|---|---|---|
| function | Ingredients | Example 2(A) | Example 2(B) |
| Active ingredient | Brimonidine Tartrate | 0.35 | 0.15 |
| Resin | Amberlite IRP 69 | 0.35 | 0.15 |
| Polymeric vehicle | Hydroxy propyl methyl cellulose | 0.3 | 0.3 |
| Polymeric vehicle | Polyvinylpyrrolidone | 1.2 | 1.2 |
| Polymeric vehicle | Carbopol 974P (carbomer) | 0.1 | 0.1 |
| Preservative | Benzalkonium Chloride | 0.02 | 0.02 |
| Chelating agent | Edetate Disodium | 0.1 | 0.1 |
| Preservative | N-Lauroylsarcosine sodium | 0.06 | 0.06 |
| Osmotic agent | Mannitol | 4.5 | 4.5 |
| pH adjusting agent | Tromethamine q.s to adjust pH to 7.4 | 0.32 | 0.32 |
| Vehicle | Water for Injection | q.s. | q.s. |

The aqueous suspension of Example 2 (A) and (B) were prepared as below: In a stainless steel (SS 316) beaker, about 15% water for injection of total batch size was taken and heated to 85° C. The specified polymeric vehicle, such as hydroxy propyl methyl cellulose (hypromellose 2910) was dispersed with high speed stiffing to obtain uniform dispersion. The stiffing was continued till temperature reached 25° C. In another stainless steel (SS 316) beaker, about 12% water for injection of total batch size was taken at 25° C. Polyvinylpyrrolidone (povidone K-90) was dispersed in water for injection with stiffing to obtain uniform dispersion. In case of Example 2, in a stainless steel (SS 316) beaker, about 10% water for injection of total batch size was taken and heated at 65° C. Carbopol 974P was dispersed in heated water for injection with stiffing. The stiffing was continued till the temperature reached 25° C. The Carbopol 974P slurry was neutralized (pH7.4) with tromethamine. The hypromellose and povidone polymer dispersions obtained above were added sequentially to the carbopol 974P phase. The polymer mixture was autoclaved at 121° C. for 20 minutes. N-lauryl sarcosine sodium was mixed in a portion of water for injection and added to the polymer phase after filtration through 0.2 micron nylon filter. Mannitol was dissolved in a portion of water for injection at 50-60° C. and benzalkonium chloride, and edetate disodium were added to form a clear solution. This solution was added to the above polymer phase. A portion of water for injection of total batch size was taken in a vessel and Amberlite IRP 69 obtained as per Example 1, was dispersed with stirring. This dispersion was autoclaved at 121° C. for 20 minutes. In another vessel, a portion of water for injection was taken and brimonidine tartrate was added with stiffing to dissolve. This solution was filtered through 0.2 micron and 0.45 micron nylon filter. Filtered brimonidine tartrate solution was added to above autoclaved Amberlite IRP 69 dispersion and stirred for 30 minutes.

The Amberlite IRP 69 & Brimonidine tartrate dispersion was added to the polymer mixture obtained above with stiffing and stiffing was continued for about 30 minutes to 1 hour. The volume of suspension was finally made up to 100% batch size. The suspension was stirred for about 60 minutes, followed by homogenization at 15000 rpm for 10 mins. The pH was adjusted with tromethamine solution to about 7.4. The viscosity of aqueous suspension of Example 2(A) was measured using Brookfield viscometer and it was found to be 19.7 cps.

Example 3-5

The aqueous suspensions of Example 3 to 5 were prepared in a similar manner as above but excluding steps of addition of HPMC and PVP.

TABLE 4

Details of the aqueous suspension of the present invention

| | | % w/v | | |
|---|---|---|---|---|
| function | Ingredients | Example 3 | Example 4 | Example 5 |
| Active ingredient | Brimonidine Tartrate | 0.35 | 0.35 | 0.35 |
| Resin | Amberlite IRP 69 | 0.35 | 0.35 | 0.35 |
| Polymeric vehicle | Carbopol 974P (carbomer) | 0.1 | 0.2 | 0.3 |
| Preservative | Benzalkonium Chloride | 0.02 | 0.02 | 0.02 |
| Chelating agent | Edetate Disodium | 0.1 | 0.1 | 0.1 |
| Preservative | N-Lauroylsarcosine sodium | 0.06 | 0.06 | 0.06 |
| Osmotic agent | Mannitol | 4.5 | 4.5 | 4.5 |
| pH adjusting agent | Tromethamine q.s to adjust pH to 7.4 | 0.3 | 0.3 | 0.3 |
| Vehicle | Water for Injection | q.s. | q.s. | q.s. |

The viscosity of aqueous suspension of Example 3 to 5 was measured using Brookfield viscometer. The viscosity was found to be 8.2 cps, 12.0 cps and 97.9 cps respectively.

Example 6

Evaluation of chemical stability was made, for which the aqueous suspension of Example 2(A) was filled in 5 ml white opaque LDPE containers. The bottles filled with suspension of Example 2(A) were subjected to accelerated stability conditions to determine storage stability during the shelf life of the product. The bottles were kept at different conditions. The bottles were kept in upright as well as 'on the side' position. The observation for assay of brimonidine is given below:

TABLE 5

Results of the stability data of the suspension stored in bottles in upright position

| Assay | Initial | 25° C./ 40% RH 6M | 30° C./ 35% RH 6M | 40° C./ 25% RH 6M |
|---|---|---|---|---|
| % Brimonidine tartrate | 101.1 | 99.58 | 96.11 | 96.91 |

17

TABLE 6

Results of the stability data of the suspension stored
in bottles & kept 'on the side' position

| Assay | Initial | 25° C./ 40% RH 6M | 30° C./ 35% RH 6M | 40° C./ 25% RH 6M |
|---|---|---|---|---|
| % brimonidine tartrate | 101.1 | 99.27 | 98.01 | 95.74 |

The results in Table 5 and Table 6 indicate that there was no significant change in assay of brimonidine after long term storage. The assay of the drug remained within specified limit and no degradation products or impurities were observed upon storage. Also there was no significant increase in related substances. The suspension according to the present invention remained chemically stable during the shelf life of the product. The suspension is room temperature stable.

Example 7

The example describes the effect of shear on the reversible clusters of drug loaded nano-resin particles suspended in Example 2(A), which decluster into individual drug-loaded nano-resin particles when subjected to shear, such as a shear resulting from blinking in the eye. This effect was measured in terms of particle size distribution, initially and upon application of shear. Procedure: The test samples were subjected to shear by placing the vials containing the suspension on bath sonicator (Model type: MC-109 and SI no-1909; Mfg. by Oscar Ultrasonic Pvt. Ltd.) and shear was applied in the form of sonication frequency of 33±3 kHz for 5 seconds and the sample was withdrawn to measure the particle size distribution. Following intervals of 1 minute each the process is repeated 5 times.

The particle size measurement was done using Malvern Mastersizer 2000, Ver.5.60, Malvern Instruments Ltd., Malvern, UK, but the analyser's sonication means were not used. The sample was only subjected to mild stiffing by a mechanical stirrer. The observations are summarized below in Table 7.

TABLE 7

Figure 9:
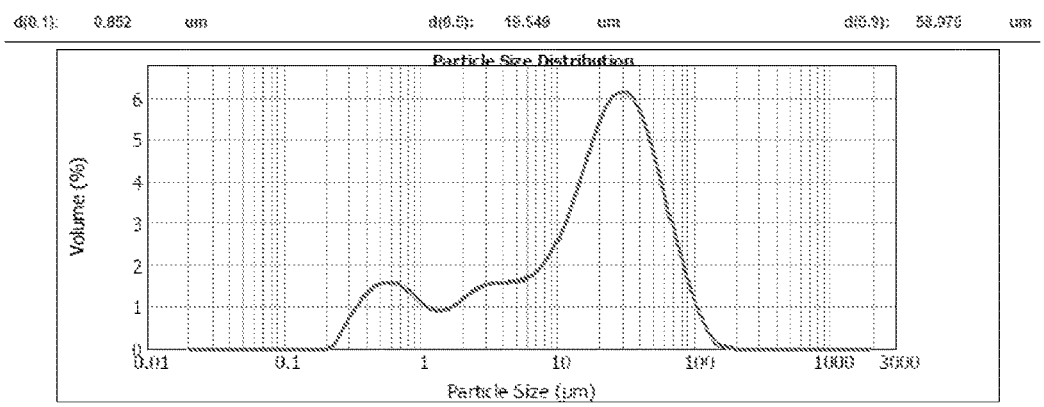
FIG. 9 is the histogram showing particle size distribution of reversible clusters/agglomerates of drug-loaded nano-resin particles prepared according to Example 2 (no shear applied). There are micron size clusters along with few nano-sized resin particles having $D_{90}$ less than 900 nm
Figure 10:
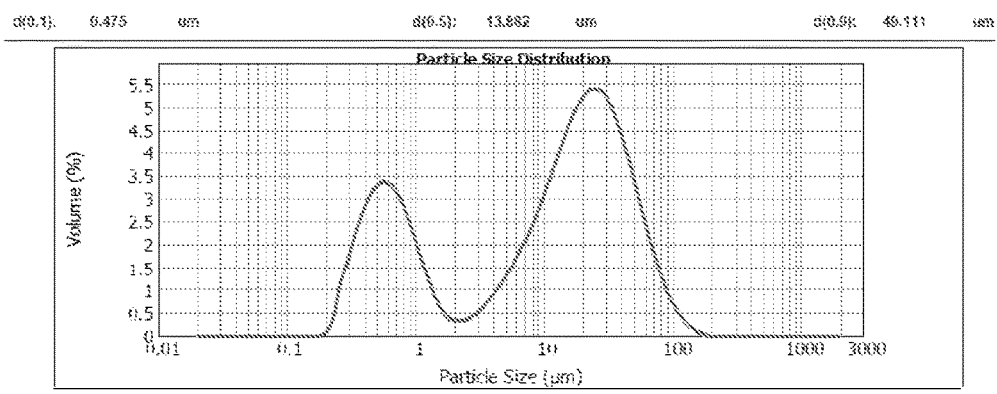
FIG. 10-14 shows histogram showing reversible clusters of drug-loaded nano-resin particles being declustered into individual drug-loaded nano-resin particles when subjected to application of shear as per Example 7 of the specification.
Figure 11:
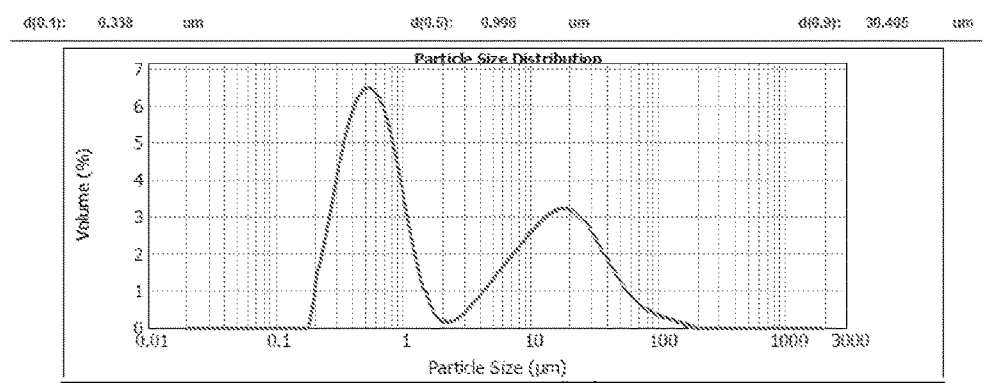
Figure 12:
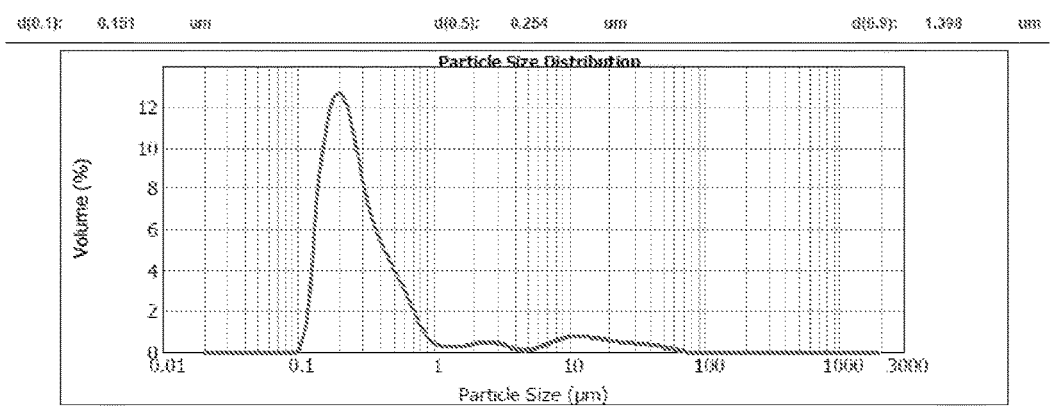
Figure 13:
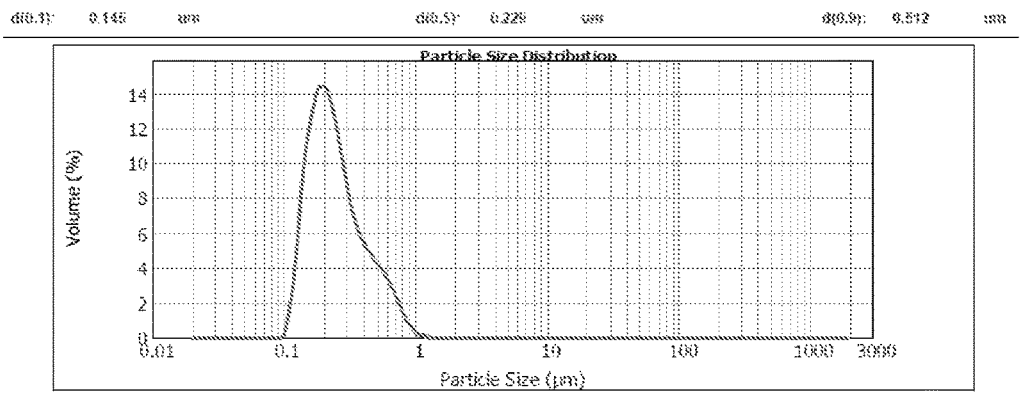
Figure 14:
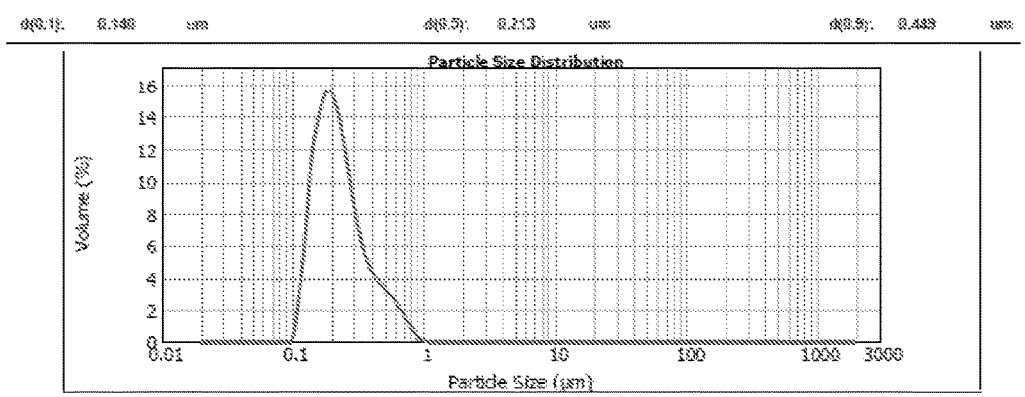

Effect of shear on the particle size distribution of the resin particles:

| | | Volume mean diameter in microns recorded by Malvern lazer diffraction method | | | | | |
|---|---|---|---|---|---|---|---|
| | | Initial | 1 min | 2 min FIG. No. | 3 min | 4 min | 5 min |
| Example No. | PSD* | FIG. 9 | FIG. 10 | FIG. 11 | FIG. 12 | FIG. 13 | FIG. 14 |
| Example 2(A) | $D_{10}$ | 0.852 | 0.475 | 0.338 | 0.151 | 0.145 | 0.140 |
| | $D_{50}$ | 19.549 | 13.882 | 0.996 | 0.254 | 0.229 | 0.213 |
| | $D_{90}$ | 58.970 | 49.111 | 30.405 | 1.398 | 0.512 | 0.449 |

PSD*—Particle Size Distribution in Volume mean diameter in microns

The histograms of the particle size distribution for suspension of Example 2(A) before sonication is depicted by FIG. 9. The suspension was then subjected to sonication at a frequency of of 33±3 KHz, for 5 seconds and a sample was withdrawn to measure the particle size distribution. The histogram of the particle size distribution upon application of first pulse of shear/sonication for 5 seconds is depicted by FIG. 10. Following intervals of one minute each, the sonication process and subsequent measurement of the particle size by Malvern, was repeated till 5 minutes. FIGS. 11 to 14, are the histograms of the particle size distribution at the end of each minute, till 5 minutes, respectively. See above table number 7 for the particle size distribution.

Observations: It was found that clusters of drug loaded nano-resin particles of Example 2(A), disintegrated completely as shear was applied to the suspension. This was evident by the decrease in the particle size observed upon application of shear/sonication as shown in Table 7 and FIGS. 9 to 14. The $D_{50}$ of drug-resin nanoparticles was initially about 19.5 microns, which upon application of shear at regular interval for 5 minutes disintegrated and converted into individual drug-resin nanoparticles having $D_{50}$ of 0.213 micron (213 nm).

FIGS. 9-14 demonstrates that particles less than 900 nms always remains, which are particles of individual drug-resin particles, while at the same time there are clusters of drug loaded nano-resin particles having $D_{50}$>2 microns, which deagglomerate into individual nano-resin particles upon application of shear. FIG. 13-14 which corresponds to application of shear at 4 and 5 minutes represents largely individual nano-resin particles and for all the purposes of the specification, are taken to represent the particle size distribution of the individual drug loaded nano-resin particles.

On the contrary, in case of Comparative Example 1 there was no disintegration and the particle size did not change. This is apparent from Table 2 and FIGS. 2 to 7. The $D_{50}$ of the suspended drug-resin particles was initially about 5.2 microns and even after application of shear at regular interval for 5 minutes, the size of the particles did not changed and remained almost the same, viz. 5.176 microns.

Example 8

The efficacy (intraocular pressure reduction effect) of the suspension of Example 2(A), administered once a day, was tested in New Zealand white (NZW) rabbits. It was compared with Alphagan®P, 0.15% w/v, which was administered three times a day and placebo which was administered once a day. Ocular hypertension was induced unilaterally (i.e. in left eye, right eye as a control) in male NZW rabbits by intravitreal injection of 0.2 ml dexamethasone (Solodex® eye drop 0.1% w/v), two injections given 10 days apart. Significant increase in intraocular pressure (>6 mmHg) compared to contralateral eye was established from day 20 of first injection of dexamethasone sustaining upto day 60; the effect of treatment with brimonidine suspension on intraocular pressure was evaluated during this period. Animals were randomized on the basis of elevated intraocular pressure to 3 different treatment groups—suspension of Example 2(A), {test} (0.35% w/v); Alphagan®P, 0.15% w/v and placebo; each group having 5 animals. The duration of dose administration was 21 days.

Figure 18:
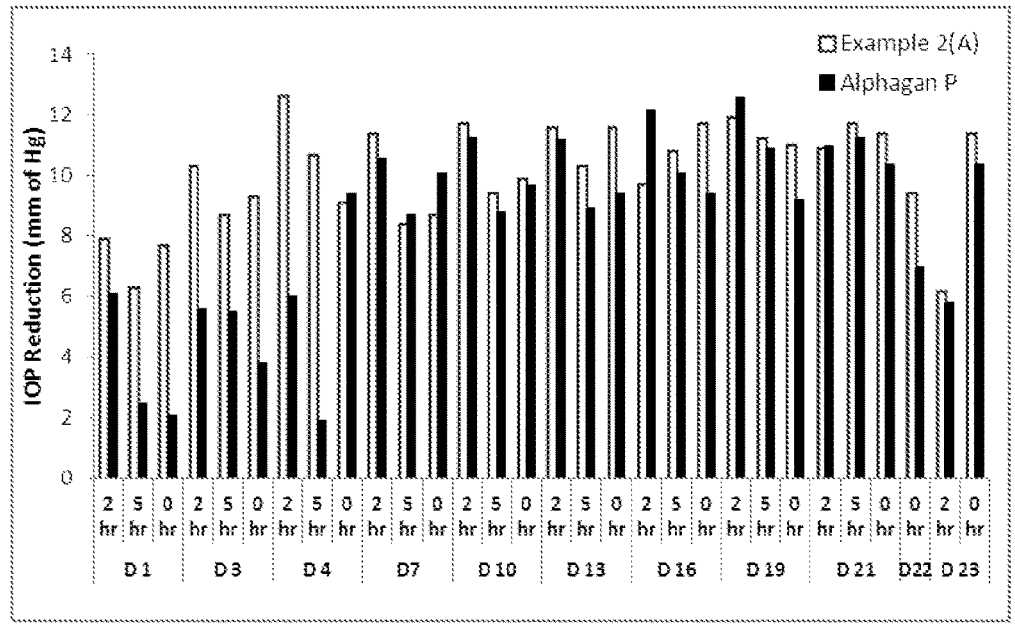
FIG. 18 provide bar graph representation of reduction in intraocular pressure (mm of Hg) upon instillation of aqueous suspension of the present invention i.e. Example 2(A); and Alphagan® P at different time points according to the study described in Example 8.

35 µl of aqueous suspension (0.35% w/v) of Example 2(A) and 35 µl of placebo were instilled once-a-day (8 a.m.) and 35 l of reference formulation Alphagan®P (brimonidine tartrate aqueous solution, 0.15% w/v) was instilled three-times-a-day (8 a.m., 2 p.m., and 8 p.m.) for 21 consecutive days. Intra ocular pressure in each eye of each animal was measured three times a day at 7 a.m. { i.e. 23 hours post dose of Example 2(A), and 11 hour post dose of Alphagan®P, represented in the figure by '0 hr'}; 10 a.m., (2 hr post dosing) and 1 p.m. (5 hr post dosing) on day 1, 3, 4, 7, 10, 13, 16, 19 and 21 during the 21-day treatment period. After discontinuation of the treatments the intra ocular pressure was measured at 7 a.m. on day 22 and at 7 a.m. and 10 a.m., on day 23. Observations for change in intra ocular pressure at different time points are presented in FIG. 18.

Observations and inference: Topical delivery of aqueous suspension of Example 2(A) to the eyes, when administered once-a-day, caused statistically significant reduction in intra ocular pressure when measured at approximately 48 hours (day 3) of its first dose. A significant reduction in intra ocular pressure was observed till day 22 i.e. 24 hours after the last dose.

Topical instillation of Alphagan® P (0.15%, three times a day) caused statistically significant reduction in IOP when measured at day 7 of its first dose (i.e.12 hrs after the last dose of day 6). A significant reduction in IOP was observed till day 21 (i.e. 5 hrs after the first dose of day 21). Reduction in IOP was not statistically significant in Alphagan®P treated group on day 13, 16, 19, and 21 at approx. 12 hrs after the last dose of previous day. It may be concluded that aqueous suspension of the present invention provided prolonged intra ocular pressure lowering effect in once-a-day dosing schedule. This effect was comparable with three times-a-day dosing of Alphagan® P (brimonidine tartrate aqueous solution, 0.15%).

Example 9

The example illustrates the method of prolonging ophthalmic action of drug 'brimonidine tartrate' to the eye, said method comprising administering the aqueous suspensions of the present invention. The efficacy (intraocular pressure reduction effect) of the suspension of Example 2(A) (having 0.35% w/v of brimonidine tartrate), administered once a day, as well as another suspension of present invention Example 2(B) (having 0.15% w/v of brimonidine tartrate), administered twice-a-day was tested in NZW rabbits. It was compared with Alphagan® P, 0.15% w/v, which is administered three times a day.

Male NZW Rabbits [5-8 months (at the time of receipt); 1.4-3.2 kg] were used for the study. On day 1, animals were divided into 4 groups as below consisting of five animals in each group.

Placebo
Brimonidine Tartrate Aqueous suspension, 0.35% w/v of Example 2 (A)—Test item 1
Brimonidine Tartrate Aqueous suspension, 0.15% w/v of Example 2(B)—Test item 2
Alphagan® P, 0.15% w/v—Reference formulation Left eye of each animal was assigned to receive respective drug solution (volume-35 μl) for the 10 days treatment periods (day 3 to day 12). Pretreatment measurements of intra ocular pressure were obtained for both the eyes of each animal at 8 AM and 6 PM for two days preceding treatment (day 1 to day 2) and 8 AM on day 3, using Pneumatonometer Model 30 Classic™ (Reichert, USA) and averaged intra ocular pressure value up to 48 hours were considered as initial (baseline) intra ocular pressure reading. During intra ocular pressure measurements, each animal was restrained in restrainer without sedation. The pneumatonometer probe was placed lightly on the cornea and allowed to rest for 10-15 seconds. The probe was placed entirely on the cornea in horizontal position and five consecutive readings were recorded, each with standard deviation value <1 which was displayed on the screen. The pneumatonometer probe filter was cleaned after each use by gently touching to cotton swab (immersed in saline) and just wiped with tissue paper. On day 3, 5, 7, 9 & 11, intra ocular pressure was measured at 8 AM and immediately after intra ocular pressure measurement, 35 μl each of placebo; test item 1; test item 2; reference item was instilled intraocularly in left eye of each respective assigned animal. Intra ocular pressure readings were measured as described above at 10 AM and 2 PM i.e. at 2 hr and 6 hr respectively post placebo/test/reference item instillation. 35 μl reference item was again instilled at 2 PM to it's group of animals. 35 μl of placebo or test item 2 or reference item was also instilled at 8 PM to its group's of animals.

Figure 19:
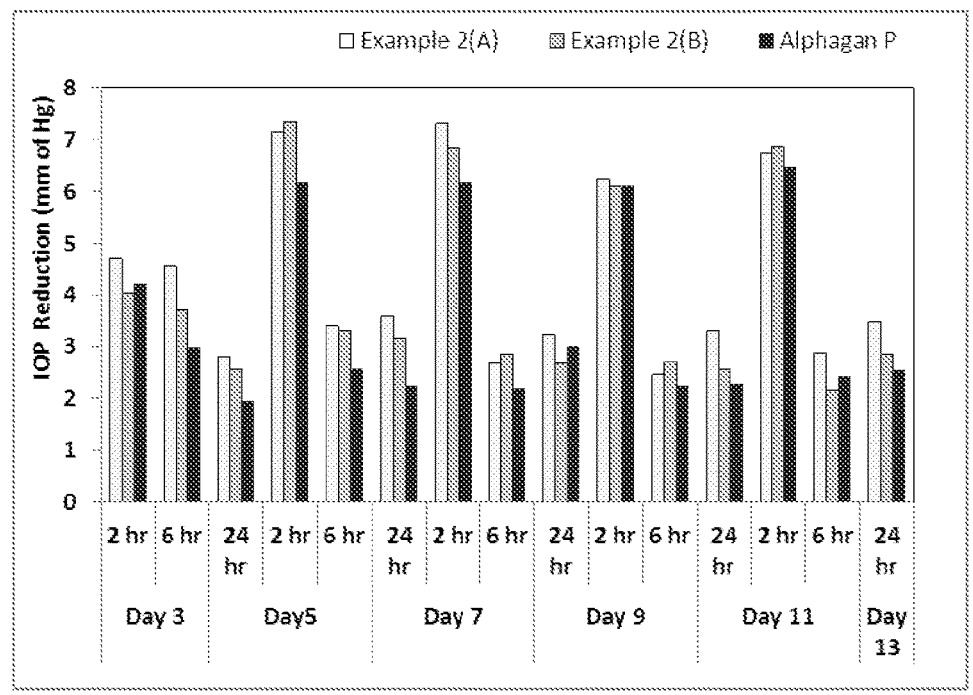
FIG. 19 provide bar graph representation of reduction in intraocular pressure (mm of Hg) upon instillation of two test formulations i.e. aqueous suspension of Example 2(A); aqueous suspension of Example 2(B); and Alphagan® P at different time points according to the study described in Example 9.

On day 4, 6, 8 & 10 at 8 AM, 35 μl of placebo or test item 1 or test item 2 or reference item was instilled intraocularly in left eye of each respective assigned animal. 35 μl reference item was again instilled at 2 PM to its group's of animals. 35 μl of placebo or test item 2 or reference item was also instilled at 8 PM to its group's of animals. On day 13 & 14, intra ocular pressure was measured at 8 AM. The % reduction in intra ocular pressure of test suspensions was calculated with respect to initial (baseline) intra ocular pressure readings of respective group. The observations for change in intra ocular pressure at different time points are presented in FIG. 19.

Observation and inference: Once a day intraocular instillation of aqueous suspension of Example 2(A) (0.35% w/v); and two times a day instillation of aqueous suspension of Example 2(B) (0.15% w/v); or three times a day instillation of Alphagan® P, showed significant reduction in baseline intra ocular pressure at 2 hr (10 AM) after first instillation on every treatment day as compared with baseline mean intra ocular pressure value. At 6 hour (2 PM) & 12 hr. (8 AM) post first instillation also showed intra ocular pressure reduction (but not significant) as compared with baseline mean intra ocular pressure. There was no statically significant difference in intra ocular pressure reduction between test item 1 or test item 2 or reference item.

Intra ocular pressure reduction potential of aqueous suspension of the present invention Example 2(A) (given once-a-day) was comparatively higher at both peak (2 hr after instillation) and trough (24 hr after instillation) than Alphagan® P (0.15%, TID). Also, the 0.15% brimonidine aqueous suspension, Example 2(B) showed comparative efficacy as compared to Alphagan® P (0.15%, TID) but at twice daily administration instead of three times a day administration as that of Alphagan P® (0.15%).

Example 10

The safety/toxicity profile of aqueous suspension comprising brimonidine tartrate (0.35% w/v) was assessed in New Zealand white rabbits following daily ocular administration for 14 days. The aim of the study was to establish NOAEL i.e. no observed adverse effect levels, exposure levels and safety criteria for ocular use in humans.

Study Design

Twenty New-Zealand White rabbits; (10 males and 10 females) were randomized, based on body weights, into following five study groups. Each group comprised of two animals of both gender. The desired dose was administered by ocular instillation.

G1 (saline {control}, 360 μL/animal/day), 30 μL per eye/time×6 times a day
G2 (Placebo, 360 μL/animal/day), 30 μL per eye/time×6 times a day
G3 (Low dose {test}, 60 μL/animal/day), 30 μL per eye/time×1 times a day
G4 (Mid dose {test}, 180 μL/animal/day); 30 μL per eye/time×3 times a day
G5 (High dose {test}, 360 μL/animal/day) 30 μL per eye/time×6 times a day G3, G4 & G5 test=0.35% w/v Brimonidine Tartrate Aqueous Suspension of the present invention (Example 2(A))

The test parameters which were evaluated included— Daily Clinical Signs and Mortality; Detailed Clinical Sign Observation; Body Weights; Ophthalmoscopy and Necroscopy. The details of these test parameters along with the results are described below. Besides this, other parameters which were also evaluated (but data not given here) include: clinical pathology, histology, biochemistry, prothrombin time and urine analysis.

Daily Clinical Signs and Mortality—Cage side observations were done, twice daily, for all animals to note clinical signs, adverse effects; including those for eyes, morbidity and mortality during the dosing period. These observations were performed once before dosing and post last dosing between 2-4 hours. Animal check to observe mortality was performed twice daily throughout study period and findings were recorded.

No mortality was observed in control, placebo as well as in test item dosed groups. During dosing period of 14 days, yellowish exudates (probably clearing of excess test item) staining the areas around both eyes was observed in G4 and G5. No other adverse clinical signs were observed.

Detailed Clinical Sign Observation—Detailed observations were performed before initiation of dosing and on Days 1, 7 and 14 post dosing. The animals were examined closely for clinical signs, general behavior or any other signs. Eyes were examined with hand-held slit lamp ophthalmoscope and findings were recorded according to Draize scoring system described in table 10 below:

TABLE 10

| Clinical Sign Observation | |
|---|---|
| Corneal opacity: degree of density (the area of corneal opacity should be noted) (maximum possible 4) | |
| No ulceration or opacity | 0 |
| Scattered or diffuse areas of opacity, details of iris clearly visible | 1 |
| Easily discernible translucent area, details of iris slightly obscured | 2 |
| Nacrous area, no details of iris visible, size of pupil barely discernible | 3 |
| Opaque cornea, iris not discernible through the opacity | 4 |
| Iris (maximum possible 2) | |
| Normal | 0 |
| Markedly deepened rugae, congestion, swelling, moderate circumcorneal hyperaemia, or injection, any of these or combination of any thereof it is still reacting to light (sluggish reaction positive) | 1 |
| No reaction to light, hemorrhage, gross destruction (any or all of these) | 2 |
| Conjunctivae (maximum possible 3) Redness (refers to palpebral and bulbar conjunctivae, excluding cornea and iris) | |
| Normal | 0 |
| Some blood vessels definitely hyperaemic (injected) | 1 |
| Diffuse, crimson color, individual vessels not easily discernible | 2 |
| Diffuse beefy red | 3 |
| Chemosis: Swelling (refer to lids and/or nictating membranes) maximum possible 4 | |
| Normal | 0 |
| Some swelling above normal | 1 |

TABLE 10-continued

| Clinical Sign Observation | |
|---|---|
| Obvious swelling with partial eversion of lids | 2 |
| Swelling with lids about half closed | 3 |
| Swelling with lids more than half closed | 4 |

During detailed clinical sign observation, no test item related adverse clinical signs were observed in any group throughout the study period. Detailed examination of eyes (including Draize scoring) did not show any adverse finding/sign. The scoring for all the animals in all groups was zero.

Ophthalmoscopy: Ophthalmoscopy was performed in all animals at initiation of dosing; thereafter it was performed on Days 7 and 14. At each observation, both eyes of animal were examined with hand held ophthalmoscope (Ophthalmoscope Heine). Observations for following were noted: Eye ball, Lacrimation, Conjunctivae, Eyelids, Sclera, Pupil reaction to light, Cornea, Iris, Anterior chamber, Lens, Vitreous body and Fundus with use of mydriatic agent. The Fluorescein-staining of cornea was done at the end of dosing on Day 14. Examination of cornea was performed with the help of ophthalmoscope.

During ophthalmoscopy, no abnormality was detected in the eye of any animal during pre-dose and on Day 7 and 14 at post-dosing. No signs of corneal damage or any other abnormality was noticed for cornea with fluorescein strip staining.

Necroscopy—On completion of dosing, all animals from G1 to G5 were necropsied on day 15. Gross pathology was noted. The cranial, thoracic and visceral cavities were opened and examined macroscopically. Eye balls, optic nerve and adnexal tissues (eyelids, accessory glands, nictitating membrane, conjunctivae and orbital muscles) were examined grossly for any macroscopic change. Microscopic evaluation of tissues were performed in G1, G2 and G5 and it was not extended to any lower group since no test item related histopathological adverse effect was noted in G5. Brain, liver, lung with main stem bronchi were peer reviewed in all animals from G1, G2 and G5.

At terminal necropsy, statistically significant increase in absolute heart weights of G2 males, relative spleen weight in G4 males and relative adrenal weight in G4 females was noted; however, these changes were not dose depended, hence not considered as test item related adverse effect. Microscopic evaluation of organs/tissues in G2 or G5 male and female animals did not show any finding that could be related to dosing of placebo or test item. The microscopic findings observed in G2 and G5 were those of incidental/spontaneous nature and comparable to that in G1. Microscopic examination of eye and its adnexal tissues/organs did not show any test item or placebo related findings. In summary—No mortality was observed for males and females of any dose group. During dosing period, yellowish exudates staining around the eyes was observed both in G4 and G5 which probably was due to clearing out of excess test item. No test item related clinical signs were observed during daily or detailed clinical sign observations. No test item related adverse changes noticed in body weights, percent body weight changes, ophthalmoscopy, hematology, biochemistry, urine, absolute organ weights and relative organ weights of males and females. In males and females, no test item related macroscopic or microscopic lesions were observed in any organ including eyes in any dose group.

It is concluded that the aqueous suspension of the method of the present invention, which contains brimonidine tartarate at a concentration of 0.35% weight by volume of the aqueous suspension, when administered as 30 μL per eye in both eyes, up to maximum 6 times per day for consecutive 14 days, did not produce any adverse effects in the eye with no local toxicity at the site of application as well as no systemic toxicity. Thus, the method of the present invention not only provides an improved efficacy in terms of reduction of intraocular pressure but was also found to be safe without any adverse effects when administered for prolonged period of time, such as 14 consecutive days or more.

Example 11

Figure 15:
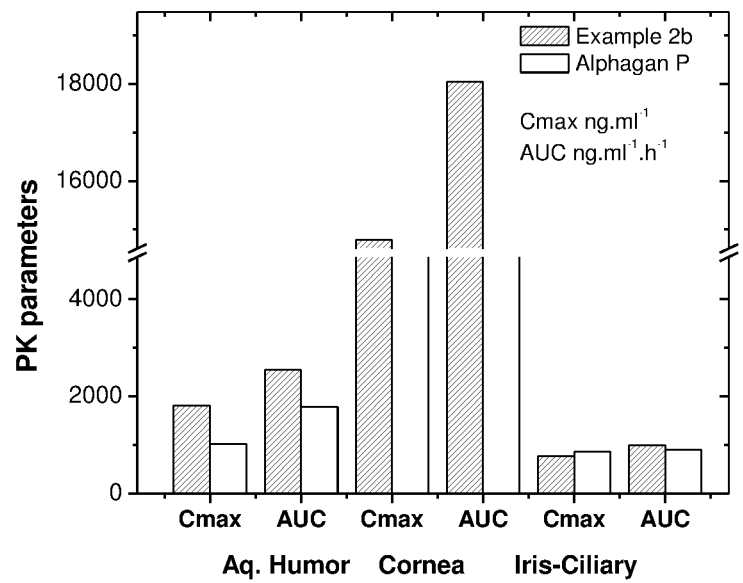
FIGS. 15-17 provides bar graph representation of values of $C_{max}$ and $AUC_{0-t}$ in different ocular tissues, obtained following ocular administration of aqueous suspension of the present invention (Example 2(B)) and reference formulation (available under the brandname: Alphagan® P), according to study described in Example 11 of the present invention.
Figure 16:
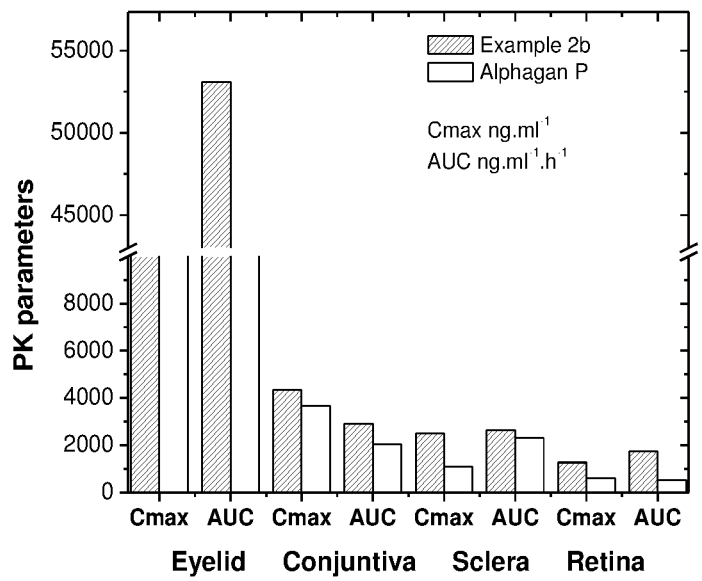
Figure 17:
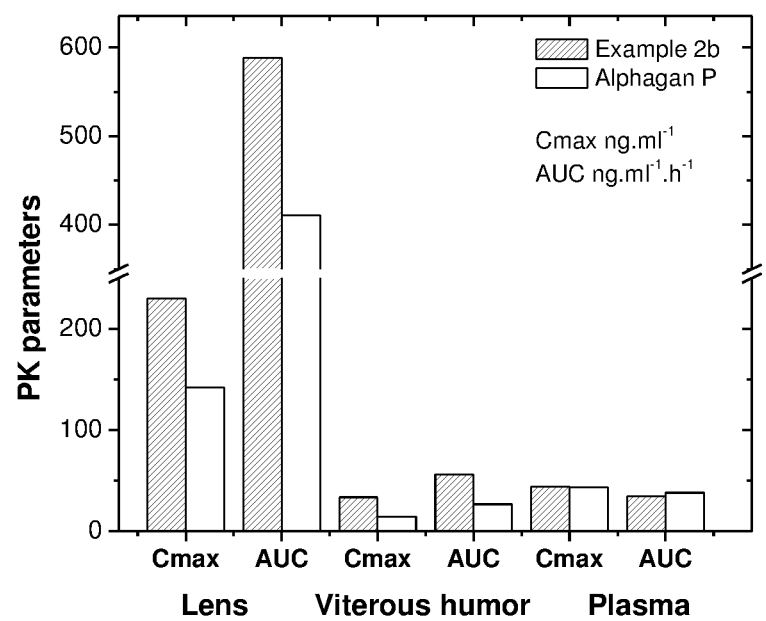

The example studies the ocular tissue distribution of ionizable drug, brimonidine tartrate upon instilling into the eye, an aqueous suspension of the present invention comprising 0.15% w/v of brimonidine tartrate (suspension of Example 2(B); called herein as test formulation), and it was compared with currently marketed product Alphagan® P having 0.15% w/v of Brimonidine Tartrate (called herein as reference formulation). The study was conducted in New Zealand white rabbits. Values of $C_{max}$ and $AUC_{0-t}$ four hours post instillation (t=4 hours) of the test and reference formulations were determined in ocular tissues of the anterior and posterior segments. The values of $C_{max}$ (ng·ml$^{-1}$) and $AUC_{0-t}$ (ng·ml$^{-1}$·hr$^{-1}$) comparing the test formulation (present invention) and reference formulation (Alphagan®P. The different tissues (aqueous humour, cornea, sclera, eye-lid, conjunctiva, lens, retina, vitreous humour) are represented in FIGS. 15 to 17. It can be clearly seen that the maximum concentration ($C_{max}$) as well as the bioavailability ($AUC_{0-t}$) is higher in all the tissues in case of test formulation, i.e. aqueous suspension of the present invention versus the reference formulation, i.e. Alphagan®P. The difference in values is significant. For instance in FIG. 15, the $C_{max}$ in cornea for test formulation is 14793 ng. ml$^{-1}$, while it is only 6491 ng. ml$^{-1}$ in it case of reference formulation. The $C_{max}$ in retina for test formulation is 1267 ng. ml$^{-1}$, while is only 603 ng. ml$^{-1}$ in case of reference formulation (FIG. 16). Also, a higher amount of drug is reaching tissues in case of test formulation; for instance the bioavailability. i.e. $AUC_{0-t}$ in the posterior segment tissue such as retina was 1741 ng. ml$^{-1}$·hr$^{-1}$ in case of test formulation versus $AUC_{0-t}$ of 537 ng. ml$^{-1}$·hr$^{-1}$ obtained for reference formulation. Thus, from the results of this study which compared equivalent strengths (0.15% w/v) of the test formulation versus the reference formulation, it is evident that the aqueous suspension of the present invention provides increased bioavailability and higher $C_{max}$ in all tissues, compared to conventional marketed formulation (Alphagan®P).

The present invention thus provides a method of increasing the bioavailability and/or prolonging ophthalmic action of a drug, the method comprising instilling into the eye an aqueous suspension comprising reversible clusters of drug loaded nano-resin particles having a particle size distribution characterized in that the $D_{90}$ value is 70 nanometer to 900 nanometers said clusters having a mean size of atleast 2 micrometers.

Example 12

TABLE 11

Aqueous suspension according to specific embodiments of the present invention comprising a combination of two ionizable drugs, brimonidine tartrate and timolol maleate

| Ingredients function | Ingredients | % w/v |
|---|---|---|
| Active ingredient | Brimonidine Tartrate | 0.1-0.35 |
| Active Ingredient | Timolol maleate equivalent to timolol | 0.5 |
| Resin | Sodium polystyrene divinyl benzene sulphonate | 0.1-0.35 |
| Polymeric vehicle | Hydroxy propyl methyl cellulose | 0.3 |
| Polymeric vehicle | Polyvinylpyrrolidone | 1.2 |
| Polymeric vehicle | Carbopol 974P (carbomer) | 0.1 |
| Preservative | Benzalkonium Chloride | 0.02 |
| Chelating agent | Edetate Disodium | 0.1 |
| Preservative | N-Lauroylsarcosine sodium | 0.06 |
| Osmotic agent | Mannitol | 4.5 |
| pH adjusting agent | Tromethamine q.s to adjust pH to 7.4 | 4.2-5.6 |
| Vehicle | Water for Injection | q.s. |

The Aqueous Suspension was Prepared as Below:

In a stainless steel (SS 316) beaker, about 15% water for injection of total batch size was taken and heated to 85° C. The specified polymeric vehicle, such as Hydroxy propyl methyl cellulose (hypromellose 2910) was dispersed with high speed stiffing to obtain uniform dispersion. The stiffing was continued till temperature reached 25° C. In another stainless steel (SS 316) beaker, about 12% water for injection of total batch size was taken at 25° C. Polyvinylpyrrolidone (povidone K-90) was dispersed in water for injection with stiffing to obtain uniform dispersion. In a stainless steel (SS 316) beaker, about 10% water for injection of total batch size was taken and heated at 65° C. Carbopol 974P was dispersed in heated water for injection with stirring. The stiffing was continued till the temperature reached 25° C. The Carbopol 974P slurry was neutralized (pH7.4) with tromethamine. The hypromellose and povidone polymer dispersions obtained above were added sequentially to the carbopol 974P phase. The polymer mixture was autoclaved at 121° C. for 20 minutes. N-lauryl sarcosine sodium was mixed in a portion of water for injection and added to the polymer phase after filtration through 0.2 micron nylon filter. Mannitol was dissolved in a portion of water for injection at 50-60° C. and benzalkonium chloride, and edetate disodium were added to form a clear solution. This solution was added to the above polymer phase. Amberlite IRP 69 was obtained as per Example 1. The particle size distribution of the milled resin was such that $D_{10}$=0.074 microns, $D_{50}$=0.153 microns and $D_{90}$=0.436 microns. The Amberlite IRP 69 nanoresin so obtained was dispersed in a portion of water for injection with stiffing. This dispersion was autoclaved at 121° C. for 20 minutes. In another vessel, about 10% of water for injection of total batch size was taken and brimonidine tartrate was added with stiffing to dissolve. This solution was filtered through 0.2 micron and 0.45 micron nylon filter. Filtered brimonidine tartrate solution was added to above autoclaved Amberlite IRP 69 dispersion and stirred for 30 minutes.

The Amberlite IRP 69 & Brimonidine tartrate dispersion was added to the polymer mixture obtained above with stiffing and stiffing was continued for 30 minutes. About 10% water for injection of total batch size was taken and Timolol maleate was added with stiffing to dissolve. This solution was filtered through 0.2 micron and 0.45 micron nylon filter. Filtered Timolol maleate solution was added to above phase and stir for 30 minutes. The pH was adjusted with tromethamine solution to about 7.4. The volume of suspension was finally made up to 100% batch size. The suspension was stirred for 60 minutes, followed by homogenization at 15000 rpm for 10 minutes.

Example 13

The example provides aqueous suspension formulation of ionizable drugs doxycycline, according to one embodiment of the present invention

TABLE 12

Doxyclycline suspension, 0.05% w/v

| Ingredients function | Ingredients | Quantity % |
|---|---|---|
| Active Ingredient | Doxycycline Hyclate (eq to Doxycycline 0.05%) | 0.057 |
| Resin | Sodium polystyrene divinyl benzene sulphonate (Amberlite IRP 69) | 0.019 |
| Polymeric vehicle | Hydroxy propyl methyl cellulose | 0.3 |
| Polymeric vehicle | Polyvinylpyrrolidone | 1.2 |
| Polymeric vehicle | Carbopol 974P (carbomer) | 0.1 |
| Preservative | Benzalkonium Chloride | 0.02 |
| Chelating agent | Edetate Disodium | 0.1 |
| Preservative | N-Lauroylsarcosine sodium | 0.06 |
| Osmotic agent | Mannitol | 4.5 |
| pH adjusting agent | Tromethamine q.s to adjust pH to 5.0 | 0.0248 |
| Vehicle | Water for Injection | q.s. to 100 |

Procedure: In a stainless steel (SS 316) beaker, water for injection was taken and heated to 85° C. The specified polymeric vehicle, such as Hydroxy propyl methyl cellulose (hypromellose 2910) was dispersed with high speed stiffing to obtain uniform dispersion. The stiffing was continued till temperature reached 25° C. In another stainless steel (SS 316) beaker, a portion of water for injection was taken at 25° C. Polyvinylpyrrolidone (povidone K-90) was dispersed in water for injection with stiffing to obtain uniform dispersion. In a stainless steel (SS 316) beaker, a portion of water for injection was taken and heated at 65° C. Carbopol 974P was dispersed in heated water for injection with stirring. The stiffing was continued till the temperature reached 25° C. The Carbopol 974P slurry was neutralized with tromethamine. The hypromellose and povidone polymer dispersions obtained above were added sequentially to the carbopol 974P phase. The polymer mixture was autoclaved at 121° C. for 20 minutes. N-lauryl sarcosine sodium was mixed in a portion of water for injection and added to the polymer phase after filtration through 0.2 micron nylon filter. Mannitol was dissolved in a portion of water for injection at 50-60° C. and benzalkonium chloride, and edetate disodium were added to form a clear solution. This solution was added to the above polymer phase. Amberlite IRP 69 was obtained as per Example 1. The particle size distribution of the milled resin was such that $D_{10}$=0.074 microns, $D_{50}$=0.153 microns and $D_{90}$=0.436 microns. The Amberlite IRP 69 nanoresin so obtained was dispersed in a portion of water for injection with stiffing. In another vessel, about 10% water for injection of total batch size was taken and doxyclycline hyclate was added with stiffing to dissolve. Filtered doxyclycline hyclate solution was added to above Amberlite IRP69 dispersion and stirred for 30 minutes. The Amberlite IRP 69 & doxyclycline hyclate dispersion was added to the polymer mixture obtained above with stiffing and stirring was continued for 1 hr. The pH was adjusted to 5.0 with tromethamine solution. The volume of suspension was finally made up to 100% batch size. The suspension was stirred for 60 minutes.

Example 14

The example provides aqueous suspension formulation of Bromfenac sodium, according to one embodiment of the present invention.

TABLE 13

Bromfenac sodium suspension 0.07% w/v

| Ingredient Function | Ingredients | Example 15 (A) % w/v | Example 15 (B) % w/v |
|---|---|---|---|
| Active Ingredient | Bromfenac sodium (equivalent to bromfenac free acid 0.07%) | 0.0805 | 0.0805 |
| Anion exchange resin | Indion ™860 | 0.07 | 0.07 |
| Polymeric vehicle | Carbopol 974 P (Carbomer) | — | 0.1 |
| Polymeric vehicle | Hydroxy propyl methyl cellulose | 0.3 | 0.3 |
| Polymeric vehicle | polyvinylpyrrolidone | 1.2 | 1.2 |
| Preservative | Benzalkonium Chloride | 0.02 | 0.02 |
| Chelating agent | Edetate Disodium | 0.1 | 0.1 |
| Preservative | N-Lauroylsarcosine sodium | 0.06 | 0.06 |
| Osmotic agent | Mannitol | 4.5 | 4.5 |
| pH adjusting agent | Tromethamine q.s to adjust pH to 7.8 | qs | qs |
| Vehicle | Water for Injection | q.s. to 100 | q.s. to 100 |

Process: In a stainless steel (SS 316) beaker, about 15% water for injection of total batch size was taken and heated to 85° C. The specified polymeric vehicle, such as hydroxy propyl methyl cellulose (hypromellose 2910) was dispersed with high speed stiffing to obtain uniform dispersion. The stiffing was continued till temperature reached 25° C. In another stainless steel (SS 316) beaker, about 12% water for injection of total batch size was taken at 25° C. Polyvinylpyrrolidone (povidone K-90) was dispersed in water for injection with stiffing to obtain uniform dispersion. In case of Example 15 (B) in a stainless steel (SS 316) beaker, about 10% water for injection of total batch size was taken and heated at 65° C. Carbopol 974P was dispersed in heated water for injection with stiffing. The stiffing was continued till the temperature reached 25° C. The Carbopol 974P slurry was neutralized (pH7.4) with tromethamine. The hypromellose and povidone polymer dispersions obtained above were added sequentially to the carbopol 974P phase. The polymer mixture was autoclaved at 121° C. for 20 minutes. N-lauryl sarcosine sodium was mixed in a portion of water for injection and added to the polymer phase after filtration through 0.2 micron nylon filter. Mannitol was dissolved in a portion of water for injection at 50-60° C. and benzalkonium chloride, and edetate disodium were added to form a clear solution. This solution was added to the above polymer phase. A portion of water for injection of total batch size was taken in a vessel and Indion™860 obtained following a process similar to Example 1, was dispersed with stiffing. This dispersion was autoclaved at 121° C. for 20 minutes. In another vessel, a portion of water for injection was taken and bromfenac sodium was added with stiffing to dissolve. This solution was filtered through 0.2 micron and 0.45 micron nylon filter. Filtered bromfenac sodium solution was added to above autoclaved Indion™860 dispersion and stirred for 30 minutes. The Indion™860 & bromfenac sodium dispersion was added to the polymer mixture obtained above with stirring and stirring was continued for about 30 minutes to 1 hour. The volume of suspension was finally made up to 100% batch size. The suspension was stirred for about 60 minutes, followed by homogenization at 15000 rpm for 10 mins. The pH was adjusted with tromethamine solution to about 7.8.

The invention claimed is:

1. A method of increasing the bioavailability and/or prolonging ophthalmic action of a drug, the method comprising instilling into the eye an aqueous suspension comprising (a) reversible clusters of drug loaded ion-exchange resin particles, said clusters have a $D_{50}$ value of at least 2 micrometer and said drug loaded ion-exchange resin particles have a particle size distribution characterized in that the $D_{90}$ value is 70 nanometers to 900 nanometers and (b) a suspending agent.

2. The method as claimed in claim 1, wherein the $D_{90}$ value is 200 nanometer to 700 nanometer.

3. The method as claimed in claim 1, wherein the drug is selected from brimonidine, doxycycline, bromfenac, olopatadine, emedastine, dorzolamide, ciprofloxacin, moxifloxacin, besifloxacin, gentamicin, neomycin, polymyxin B, ketotifen, phenylephrine, pyrilamine, dipivefrin, oxymetazoline, levocabastine, azelastine, epinastine, bepotastine, dipivefrin, naphazoline, apraclonidine, levobunolol, betaxolol, levobetaxolol, timolol, carteolol, dextromethorphan, cyclopentolate, proparacaine, pilocarpine, diclofenac, sulfacetamide, flurbiprofen, ketorolac or their pharmaceutically acceptable salts or mixtures thereof.

4. The method as claimed in claim 3, wherein the drug is brimonidine or its pharmaceutically acceptable salt and is present at a concentration of 0.05% to 0.5% weight by volume.

5. The method as claimed in claim 4, wherein brimonidine or its pharmaceutically acceptable salt is brimonidine tartarate and it is present at a concentration of 0.35% weight by volume.

6. The method as claimed in claim 1, wherein the drug loaded ion-exchange resin particles have a particle size distribution characterized in that the D50 value is 50 nanometer to 350 nanometer.

7. The method as claimed in claim 1, wherein the ion-exchange resin is selected from a cation exchange nano-resin or an anion exchange nano-resin.

8. The method as claimed in claim 7, wherein the cation exchange nano-resin is polystyrene divinyl benzene sulfonate.

9. The method as claimed in claim 1, wherein the suspending agent is selected from an anionic polymer, a non-ionic polymer or mixtures thereof.

10. The method as claimed in claim 5, wherein the aqueous suspension is instilled into the eye once-a-day for the treatment of glaucoma.

11. An aqueous suspension comprising (a) reversible clusters of drug loaded ion-exchange resin particles, said clusters have a $D_{50}$ value of at least 2 micrometers and said drug loaded ion-exchange resin particles have a particle size distribution characterized in that the $D_{90}$ value is 70 nanometers to 900 nanometers, and (b) a suspending agent.

12. The aqueous suspension as claimed in claim 11, wherein the $D_{90}$ value is 200 nanometers to 700 nanometers.

13. The aqueous suspension as claimed in claim 11, wherein the drug is selected from brimonidine, doxycycline, bromfenac, olopatadine, emedastine, dorzolamide, ciprofloxacin, moxifloxacin, besifloxacin, gentamicin, neomycin, polymyxin B, ketotifen, phenylephrine, pyrilamine, dipivefrin, oxymetazoline, levocabastine, azelastine, epinastine, bepotastine, dipivefrin, naphazoline, apraclonidine, levobunolol, betaxolol, levobetaxolol, timolol, carteolol, dextromethorphan, cyclopentolate, proparacaine, pilocarpine, diclofenac, sulfacetamide, flurbiprofen, ketorolac or their pharmaceutically acceptable salts or mixtures thereof.

14. The aqueous suspension as claimed in claim 13, wherein the drug is brimonidine or its pharmaceutically acceptable salt and is present at a concentration of 0.05% to 0.5% weight by volume.

15. The aqueous suspension as claimed in claim 14, wherein brimonidine or its pharmaceutically acceptable salt is brimonidine tartarate and it is present at a concentration of 0.35% weight by volume.

16. The aqueous suspension as claimed in claim 11, wherein the drug loaded ion-exchange resin particles have a particle size distribution characterized in that the D50 value is 50 nanometers to 350 nanometers.

17. The aqueous suspension as claimed in claim 11, wherein the ion-exchange resin is selected from a cation exchange nano-resin or an anion exchange nano-resin.

18. The aqueous suspension as claimed in claim 17, wherein the cation exchange nano-resin is polystyrene divinyl benzene sulfonate.

19. The aqueous suspension as claimed in claim 11, wherein the suspending agent is selected from an anionic polymer, a non-ionic polymer or mixtures thereof.

* * * * *